(12) United States Patent
Battlogg

(10) Patent No.: US 11,439,521 B2
(45) Date of Patent: Sep. 13, 2022

(54) PROSTHESIS DEVICE WITH A ROTARY DAMPER

(71) Applicant: INVENTUS ENGINEERING GMBH, St. Anton i.M. (AT)

(72) Inventor: Stefan Battlogg, St. Anton i.M. (AT)

(73) Assignee: INVENTUS Engineering GmbH, St Anton i.M. (AT)

( * ) Notice: Subject to any disclaimer, the term of this patent is extended or adjusted under 35 U.S.C. 154(b) by 305 days.

(21) Appl. No.: 16/488,686

(22) PCT Filed: Feb. 26, 2018

(86) PCT No.: PCT/EP2018/054685
§ 371 (c)(1),
(2) Date: Aug. 26, 2019

(87) PCT Pub. No.: WO2018/154117
PCT Pub. Date: Aug. 30, 2018

(65) Prior Publication Data
US 2021/0251781 A1   Aug. 19, 2021

(30) Foreign Application Priority Data

Feb. 24, 2017 (DE) ...................... 10 2017 103 809.4

(51) Int. Cl.
*A61F 2/70* (2006.01)
*F16F 9/53* (2006.01)
(Continued)

(52) U.S. Cl.
CPC .................. *A61F 2/70* (2013.01); *A61F 2/54* (2013.01); *A61F 2/60* (2013.01); *A61F 2/64* (2013.01);
(Continued)

(58) Field of Classification Search
CPC .............. A61F 2002/5004; A61F 2/744; A61F 2002/5003; A61F 2002/5006; A61F 2002/5033
See application file for complete search history.

(56) References Cited

U.S. PATENT DOCUMENTS 5,810,129 A   9/1998 Hanawa et al.
6,318,522 B1  11/2001 Johnston et al.
(Continued)

FOREIGN PATENT DOCUMENTS

CN   1715703 A    1/2006
CN   102979847 A  3/2013
(Continued)

*Primary Examiner* — David H Willse
(74) *Attorney, Agent, or Firm* — Laurence A. Greenberg; Werner H. Stemer; Ralph E. Locher

(57) ABSTRACT

A prosthesis device has a rotary damper and a displacing device with a magnetorheological fluid in a damper volume of a housing. Two partition units divide the damper volume into two or more variable chambers. The partition units include a partition wall connected with the housing and a partition wall connected with a damper shaft. Radial gaps are formed in the radial direction between the partition wall on the housing and the damper shaft, and between the partition wall on the damper shaft and the housing. An axial gap is formed in the axial direction between the partition unit, the damper shaft and the housing. The magnetic field of the magnetic field source passes through at least two of the gaps.

18 Claims, 9 Drawing Sheets

(51) Int. Cl.
*A61F 2/74* (2006.01)
*F16F 9/12* (2006.01)
*A61F 2/64* (2006.01)
*A61F 2/54* (2006.01)
*A61F 2/60* (2006.01)
*A61F 2/50* (2006.01)
*A61F 2/76* (2006.01)

(52) U.S. Cl.
CPC .............. *A61F 2/744* (2021.08); *A61F 2/748* (2021.08); *F16F 9/12* (2013.01); *F16F 9/535* (2013.01); *A61F 2002/5004* (2013.01); *A61F 2002/5033* (2013.01); *A61F 2002/762* (2013.01); *A61F 2002/7625* (2013.01); *A61F 2002/7665* (2013.01); *F16F 2222/06* (2013.01); *F16F 2224/045* (2013.01); *F16F 2232/02* (2013.01)

(56) References Cited

U.S. PATENT DOCUMENTS

| | | | |
|---|---|---|---|
| 6,764,520 | B2 | 7/2004 | Deffenbaugh et al. |
| 7,278,522 | B2 | 10/2007 | Reinhardt et al. |
| 9,091,309 | B2 | 7/2015 | Battlogg |
| 9,399,495 | B2 | 7/2016 | Pierini et al. |
| 2004/0054423 | A1 | 3/2004 | Martin |
| 2009/0030530 | A1* | 1/2009 | Martin .................. A61F 2/6607 623/53 |
| 2009/0183959 | A1 | 7/2009 | Klit et al. |
| 2010/0160844 | A1 | 6/2010 | Gilbert et al. |
| 2011/0045932 | A1* | 2/2011 | Fauteux .................. B25J 9/102 475/221 |
| 2015/0285326 | A1 | 10/2015 | Battlogg et al. |
| 2016/0009158 | A1 | 1/2016 | Baasch et al. |
| 2016/0302956 | A1 | 10/2016 | Gilbert et al. |
| 2019/0111300 | A1 | 4/2019 | Battlogg |

FOREIGN PATENT DOCUMENTS

| | | |
|---|---|---|
| CN | 105570374 A | 5/2016 |
| DE | 60112403 T2 | 6/2006 |
| DE | 60309685 T2 | 9/2007 |
| DE | 102010055833 A1 | 3/2012 |
| DE | 102012016948 A1 | 3/2014 |
| DE | 102013203331 A1 | 8/2014 |
| DE | 102015104927 A1 | 10/2016 |
| EP | 0769636 A2 | 4/1997 |
| EP | 1531283 A1 | 5/2005 |
| EP | 2875255 B1 | 11/2016 |
| JP | H08177939 A | 7/1996 |
| JP | 2005172096 A | 6/2005 |
| JP | 2005331107 A | 12/2005 |
| JP | 2007139083 A | 6/2007 |
| JP | 2009287639 A | 12/2009 |
| WO | 2014013435 A1 | 1/2014 |

* cited by examiner

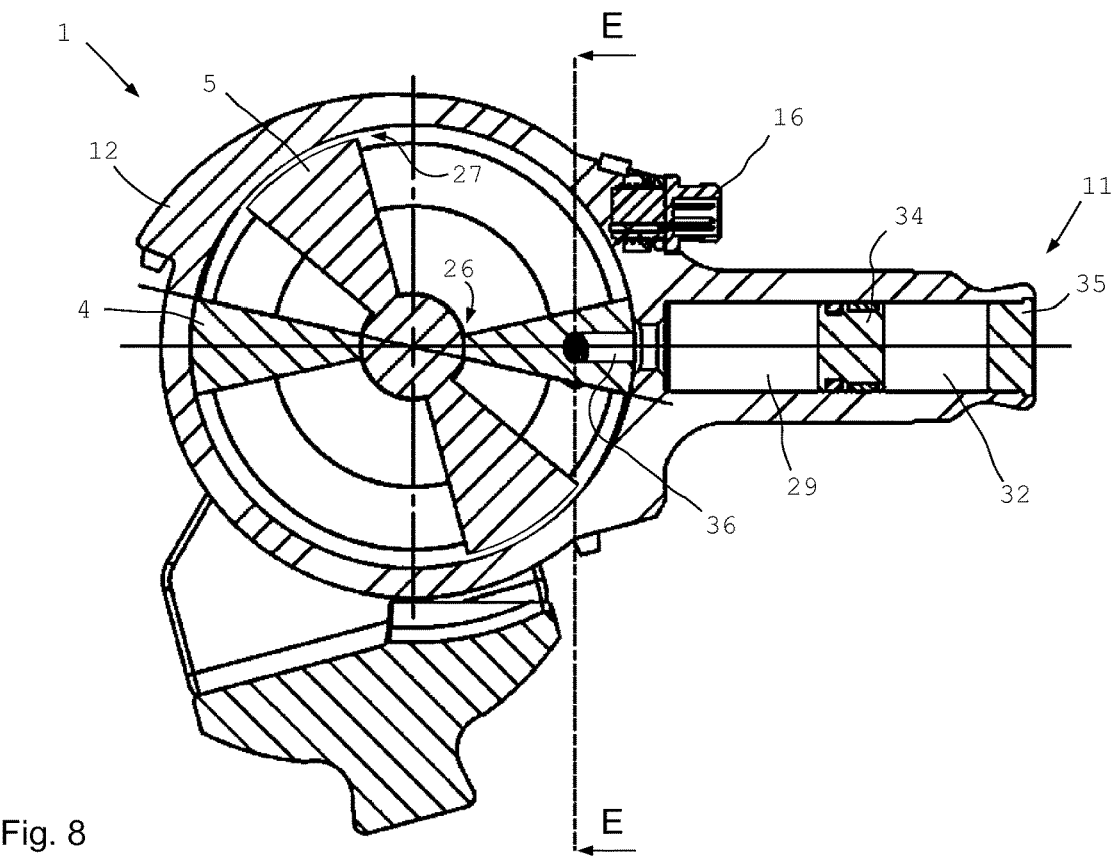
Fig. 8
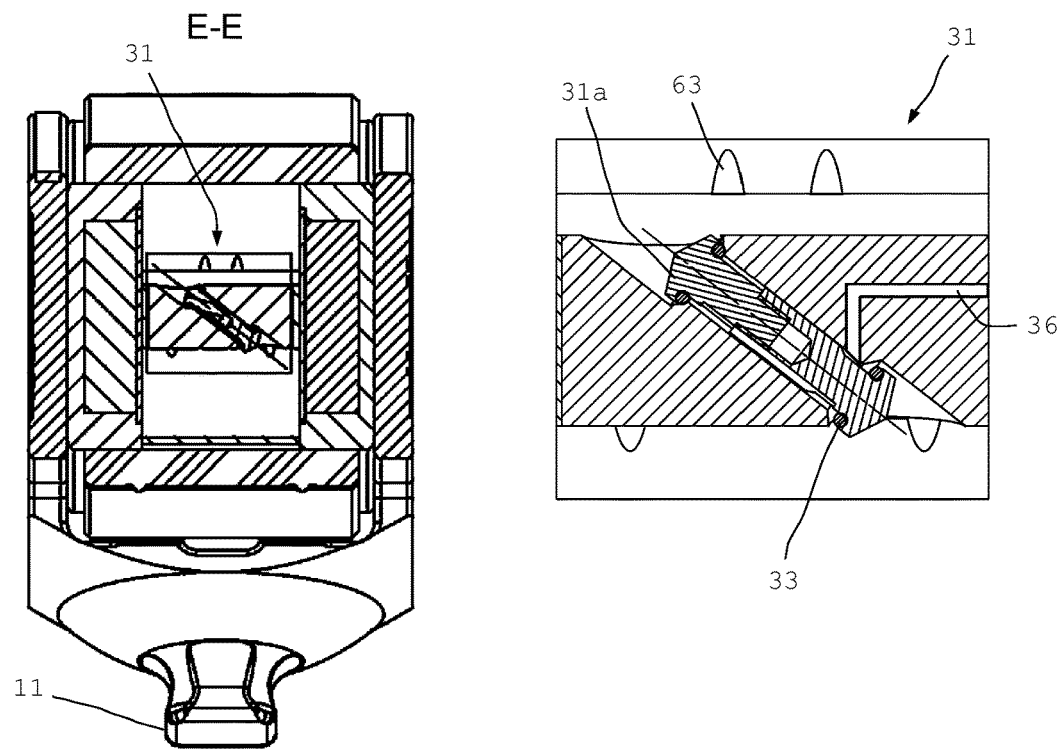
Fig. 9 — Fig. 10

PROSTHESIS DEVICE WITH A ROTARY DAMPER

BACKGROUND OF THE INVENTION

Field of the Invention

The present invention relates to a prosthesis device with a rotary damper, the rotary damper comprising a housing and a damper shaft rotatably accommodated thereat and a displacing device in the housing. In the housing a damper volume comprising magnetorheological fluid is provided as a working fluid for influencing the damping of the rotary or pivoting motion of the damper shaft relative to the housing.

The prior art has disclosed a great variety of prosthesis devices with dampers which enable damping a pivoting motion e.g. of a knee. In particular in knee prosthesis devices the required or desired braking momentum is relatively high to ensure a safe and comfortable function. Since with prosthesis devices the required and available rotation angle or pivot angle is limited, many of the known rotary dampers are not sufficiently flexible in application or the required braking momentum is too weak so that the braking momentum cannot be varied as fast as required or cannot be set strong.

Rotation dampers involving oil and external control valves are prior art. Minimum space requirement is of considerable advantage in particular in the case of prosthesis devices but in other applications as well. This means that the active surfaces are small and this is why the working pressure must be increased (100 bar and more) for generating suitable surface pressures and thus, forces or moments. A drawback of these actuators is that the parts moving relative to one another must be manufactured with high precision so any gaps must provide the highest possible pressure drop and thus a sealing effect is achieved. These narrow gap dimensions and narrow tolerances in sliding pairs increase the hydraulic and mechanical base friction/moments, involving unfavorable effects on functionality and responsivity. Another consequence is the expectation of high mechanical wear and short service intervals. Since this tends to include inner contours and rectangular or deformed components/sealing edges which must preferably be ground to achieve good tolerances/gaps, very high costs are involved. Given these contours, pressures, alternatively attaching sealing members likewise involves lots of work and costs. Sealing the edges or transitions e.g. between axial and radial contours is particularly difficult. Moreover, seals lead to high base frictions or base friction forces and moments.

SUMMARY OF THE INVENTION

It is therefore the object of the present invention to provide a prosthesis device with a rotary damper of a simple structure which enables flexibility in setting the damping and allows damping high and weak forces and rotational forces.

This object is solved by a prosthesis device with a rotary damper having the features as claimed. Preferred specific embodiments of the invention are the subjects of the dependent claims. Further advantages and features of the present invention can be taken from the general description and the description of the exemplary embodiments.

A prosthesis device according to the invention comprises a housing and a damper shaft rotatably accommodated thereon, a displacing device in the housing and at least one magnetic field source. The displacing device has a damper volume with magnetorheological fluid as a working fluid by means of which it can operate to influence the damping of the rotary motion of the damper shaft relative to the housing. The displacing device comprises at least two partition units which subdivide the damper volume or a damper volume in the damper housing into at least two variable chambers, at least one of the partition units comprising a partition wall connected with the housing. At least one of the partition units comprises a partition wall connected with the damper shaft and may preferably be configured as a swiveling vane. In the radial direction a (first) (radial) gap section or gap is configured between the partition unit connected with the housing and the damper shaft. The first gap section substantially extends in the axial direction. In the radial direction another (or a second) (radial) gap section is configured between the partition unit connected with the damper shaft and the housing. The other or second gap section extends at least over a considerable portion in the axial direction. In the axial direction at least one more (or a third) (axial) gap section is configured between the partition unit connected with the damper shaft and the housing. This (i.e. the third gap section) extends at least over a considerable portion in the radial direction. At least a substantial part of the magnetic field of the magnetic field source passes through at least two of the indicated gap sections.

Each gap section may be configured as a separate gap or two or more gap sections may be part of one shared gap.

Each gap section shows a direction of extension or direction of curve and a gap height transverse to the direction of curve. A purely axial gap section extends in the radial direction and/or the peripheral direction. The gap height extends in the axial direction. A purely radial gap section extends in the axial direction and optionally also in the peripheral direction.

Then the first and the second gap sections particularly preferably substantially extend in the axial direction while the gap heights substantially extend in the radial direction. The third gap section is particularly preferably configured as an axial gap section so that the gap height substantially extends in the axial direction. The gap section, however, substantially extends in the radial direction and/or in the peripheral direction.

The gaps or gap sections may each be linear in configuration. Alternately each gap section may show one or more bends or may consist of bent gap regions only.

The prosthesis device according to the invention has many advantages. A considerable advantage of the prosthesis device according to the invention consists in the fact that two or more gap sections and preferably all of the gap sections in the rotary damper are sealed as required by means of the magnetic field of the magnetic field source. This allows to configure the gaps or gap sections to show a sufficient gap height to provide a weak base friction. While the magnetic field is active, a high level of sealing continues to be achieved so as to enable high damping values. It is not necessary to choose a particularly low gap height to prevent leakage. Leakage is not prevented by means of the gap dimensions (gap height) but by means of magnetic sealing.

In prosthesis devices with conventional seals in pure oil circuits the gap dimension chosen must be particularly small for obtaining a high level of sealing. This simultaneously also results in a high base momentum in idling and correspondingly high wear to the seals. This is prevented according to the invention.

Preferably the magnetic field source comprises at least one controllable electric coil for influencing the strength of the magnetic field. Thus, the strength of damping and preferably also the strength of sealing is influenced. In particular a substantial part of the magnetic field of the magnetic field source passes through at least the two gap sections, simultaneously influencing at least the two gap sections indicated in dependence on the strength of the magnetic field.

An adjustable strength of the magnetic field allows to adaptively accommodate the damping strength.

A controllable electric coil allows flexibility in setting a magnetic field to the desired strength. In this way a damping at the desired strength is set. At the same time, in this way in particular the strength of sealing is set for at least two gaps and in particular all the radial and axial gaps. The base friction is weak while the magnetic field is weak, and sealing is strong while the relative pressure or the rotational force is strong. Thus, the dynamics provided can be much higher than in the prior art since not only the damping proper is influenced but so is the sealing.

In fact, a braking momentum acts which is additively combined from the existing base momentum and the damping momentum. Both the base momentum and damping momentum are influenced by the effective (temporally dependent and temporally controllable) magnetic field. In the case of weak forces and moments to be damped, a weaker force of the magnetic field generates a weaker base friction (base momentum). In the case of stronger forces and moments to be damped, a stronger force of the magnetic field generates a stronger base friction (base momentum). A stronger base momentum does not show any adverse effects on responsivity if a correspondingly stronger braking momentum is given. In particular the ratio of the braking momentum to a base momentum in a medium operating range (in particular exactly in the middle) is higher than 2:1 and preferably higher than 5:1 and particularly preferably higher than 10:1.

In a particularly preferred configuration each of the gap sections is configured as a gap. The gaps may partially merge into one another or may be configured separate from one another. Then the term gap section may be consistently replaced by the term gap in the present application.

A prosthesis device in the sense of the present invention is understood to mean not only a prosthesis but includes an exoskeleton device or an orthosis device and in particular an exoskeleton or an orthosis.

In a preferred configuration a substantial part of the magnetic field of the magnetic field source passes through at least one and in particular two axial gap sections formed at opposite ends between the housing and at least one of the partition units for sealing the lateral axial gaps. Through the magnetic field passing therethrough the magnetorheological particles present in the axial gap are interlinked so as to obtain complete sealing that is also effective with high pressures. Alternatively or additionally the magnetic field may be applied to at least one radial gap section or gap between the partition unit connected with the damper shaft and the housing so that when the magnetic field is active this radial gap (gap section) is sealed as well.

In a preferred specific embodiment at least one of the gap sections is configured as a damping gap and at least one of the gap sections, as a sealing gap. At least one of the damping gaps preferably shows a (considerably) larger gap height than does a sealing gap. The gap height of the damping gap is in particular at least double the size or at least 4 times the size or at least 8 times the size of the gap height of a sealing gap. It is preferred for the gap height of a sealing gap to be larger than 10 μm and in particular larger than 20 μm and preferably between approximately 20 μm and 50 μm. The gap height of a damping gap, however, is preferably >100 μm and preferably >250 μm and it is preferably between 200 μm and 2 mm gap height. In advantageous configurations the gap height of a damping gap may be between (approximately) 500 μm and 1 mm.

Basically all of the gap sections contribute to, or influence, the damping. The passage through a damping gap (showing a larger gap height) may be effectively controlled by a control device so as to provide for precise adjustment of the active braking momentum. A damping gap showing a larger gap height allows to convey a correspondingly high volume flow.

Preferably the magnetic field source comprises at least one electric coil. It is also possible to use two, three or more electric coils for forming the magnetic field of the magnetic field source. It is also possible for the magnetic field source to comprise at least one permanent magnet or for at least one permanent magnet to be attributed to the magnetic field source.

In preferred specific embodiments both of the axial ends of the partition wall connected with the damper shaft are each configured with a (front-face) axial gap section respectively gap between the housing and the partition wall. Preferably at least a substantial part of the magnetic field of the magnetic field source passes through both of the axial gap sections between the housing and the partition wall and provides for sealing the two (front-face) axial gap sections. These gap sections then form the third gap section and a fourth gap section. Then the axial gaps on both front faces are sealed by the magnetic field. Passage control may also be influenced by controlling the strength of the magnetic field at these sealing gaps. However, passage is decisively influenced by the one or more damping gaps or damping gap sections.

It is also possible to use a non-rectangular partition unit. The partition units may for example be semicircular and be accommodated in a corresponding hemispherical accommodation in the housing. Then, gaps or gap sections will also ensue in a (partially or predominantly) axial orientation and in a (partially or predominantly) vertical orientation. In the sense of the present invention two gap sections may also be understood to mean sections of different orientations in a continuous gap.

Preferably two electric coils are provided which are in particular each disposed adjacent to the damper volume. Preferably one controllable electric coil is associated with one axial gap each. In particular one controllable electric coil each is accommodated axially outwardly in the vicinity of an axial gap.

In all the configurations it is preferred for the magnetic field to extend transverse to at least one of the gap sections. In particular the magnetic field extends transverse to at least two, three or more gap sections. A magnetic field extending transverse to the gap section achieves a particularly strong effect. Then the magnetic field may be oriented perpendicular to the gap section. Alternately the magnetic field may extend inclined through the gap section.

It is preferred for at least one radial gap section to be configured as a damping duct and to be radially disposed between the partition unit connected with the damper shaft and the housing. It is also possible and preferred for at least one axial gap section to be configured as a damping duct and to be disposed axially between the partition unit connected with the damper shaft and the housing.

Particularly preferably both the axial gaps and the radial gaps are sealed by means of the magnetic field of the magnetic field source.

Preferably at least a substantial part of the magnetic field of the magnetic field source passes through the damping duct. Particularly preferably at least a substantial part of the magnetic field of the magnetic field source passes through all of the gap sections. A "substantial part" of the magnetic field is in particular understood to mean a proportion of >10% and preferably a proportion of more than 25%.

In all the configurations it is also possible for at least one gap section to be sealed by means of a mechanical seal. It is the object of the seal to prevent or delimit mass transfer and pressure loss/pressure drop between spaces. Such a mechanical sealant may be a mechanical seal such as a sealing lip, sealing strip, gasket, profiled gasket, brush seal, or an O-ring or quadring or the like. For example the gap section extending between the partition unit connected with the housing and the damper shaft may be sealed by a mechanical sealant while the gap section between the partition unit connected with the damper shaft and the housing and the axial gap sections are subjected to the magnetic field of the magnetic field source for setting the desired damping.

In all the configurations it is particularly preferred for the housing to comprise a first and a second end part and in-between, a center part. In particular the center part may consist of two or more separate sections. In particular at least one of the two end parts and in particular both of the end parts accommodate one electric coil each. The axis of the coil is in particular oriented substantially in parallel to the damper shaft. This achieves a compact structure which allows to obtain a high level of sealing by means of the magnetic field of the magnetic field source. A compact structure of dampers of prosthesis devices is very advantageous.

Preferably the housing consists at least substantially of a magnetically conductive material showing relative permeability of above 100. The relative permeability is in particular above 500 or above 1000. It is possible for the housing to consist entirely, or substantially, or at least for a substantial part, of such a material. Particularly preferably at least one of the housing sections adjacent to the damper volume consists of a magnetically conductive material.

Preferably a (separate) ring is disposed axially adjacent to the electric coil in the housing. The ring is in particular disposed axially between the electric coil and the damper volume.

It is possible for the ring and/or the electric coil to be located substantially, or nearly completely, or completely, radially further outwardly than the damper volume. Preferably the ring is located axially adjacent to and bordering a center part of the housing. In these configurations it is preferred for the ring to consist at least substantially or entirely of a material showing relative permeability of less than 10. The relative permeability of the ring material is in particular less than 5 or even less than 2. The ring thus preferably consists of magnetically non-conductive materials. The ring may for example consist of austenitic steel. The ring material shows magnetic permeability so as to reliably prohibit magnetic short-circuits of the magnetic field of the magnetic field source. In these configurations the ring is in particular configured as a flat washer or a hollow cylinder.

In other configurations the ring and/or the electric coil is disposed (substantially) not adjacent to the center part of the housing. Then it is possible and preferred for the ring and/or the electric coil to be disposed radially further inwardly and/or at least partially or entirely adjacent to the damper volume. The ring may be configured as a hollow cylinder and in particular as a hollow cone frustum. Then the ring shows radially outwardly a thinner wall thickness than it does radially farther inwardly. The cross-section of the ring shows an inclined orientation. In these configurations the ring preferably consists of a magnetically conductive material. Then the relative permeability of the ring material is preferably above 10 and particularly preferably above 50 and in particular above 100. The configuration is very advantageous since it allows to reliably prevent leakage through the (axial) gap section in the region of the electric coil. The ring preferably shows the shape of a cone frustum with a hollow cylindrical interior and consists of a magnetically conductive material. With such a configuration an arrangement of the coil laterally adjacent the damper volume prevents leakage in the region of the coil, in particular with an active magnetic field that is sufficiently strong to magnetically saturate the ring material.

In all the configurations a magnetic sealing of the axial gaps on the front faces increases damping. Moreover, pressure loss within the axial gap due to transfer of magnetorheological fluid is prevented.

In all the configurations it is particularly preferred to convey the magnetorheological fluid by way of relative pivoting motion of the damper shaft and of the housing through at least one (damping) gap from one chamber into the other chamber.

It is possible and preferred for the damper shaft to show two or more partition units disposed distributed over the circumference. Then preferably two or more partition units are correspondingly configured on the housing distributed over the circumference. Preferably the one partition unit connected with the damper shaft interacts with a partition unit connected with the housing. A plurality of pairs of partition units allows to increase the maximally effective braking momentum.

If only one partition unit is configured on the damper shaft and only one partition unit is configured on the housing, the maximally feasible swiveling angle between the damper shaft and the housing is as a rule less than 360° or amounts to (almost) 360°. If two partition units each are used, the maximum swiveling angle is up to (and as a rule slightly less than) 180°. Accordingly, given four partition units on the damper shaft and the housing, swiveling angles of less than 90° or up to 90° are feasible as a rule which is as a rule sufficient for prosthesis devices for knee joints. If high braking moments are required, a prosthesis device can thus be provided using simple means.

Preferably, given a pertaining number of partition units, a corresponding number of chambers or pairs of chambers are formed wherein one part thereof forms a high pressure chamber in a swiveling motion while another part thereof forms a low pressure chamber. Then the high pressure and low pressure chambers are preferably interconnected through suitable connection ducts to thus provide at all times pressure compensation between the individual high pressure chambers respectively the individual low pressure chambers. The effectiveness of the entire rotary damper is not affected by these connection ducts since in theory an identical pressure is intended to prevail at all times in all the high pressure chambers (low pressure chambers). It has been found, however, that suitable connection ducts allow to improve functionality and tolerances if any can be compensated.

In preferred configurations an equalizing device with an equalizing volume is provided. The equalizing device serves in particular to enable leakage and/or temperature compensation. The equalizing device allows to provide for volume compensation in the case of varying temperatures. Moreover an improved long-time functionality can be ensured since a suitable equalizing volume also allows compensation of leakage loss over extended periods of time without adversely affecting functionality.

In preferred configurations of all the embodiments and configurations described above the equalizing volume is connected with the two chambers (high pressure side and low pressure side) through a valve unit. The valve unit is preferably configured to establish a connection between the equalizing volume and a low pressure chamber and to block a connection between the equalizing volume and the high pressure chamber. In simple configurations this functionality is provided by a double-acting valve of a valve unit wherein both of the valves of the valve unit close if in the adjacent chamber a higher pressure prevails than in the equalizing volume. This results in automatic conveying of volume out of the equalizing volume respectively into the equalizing volume as the pressure in the pertaining low pressure chamber decreases or increases.

In particularly preferred configurations the or a part of the equalizing device is accommodated in the interior of the damper shaft. This saves mounting space. This tends to be narrow in many prostheses. In particular does the damper shaft comprise a hollow space in its interior. The hollow space is preferably accessible from (at least) one axial end of the damper shaft. In particular at least part of the hollow space or the entire hollow space is formed as a round or evenly configured hollow cylinder. Preferably a raceway for a dividing piston is configured in the hollow space or hollow cylinder to separate an air chamber or fluid chamber from an equalizing volume in particular filled with MRF. The equalizing volume is preferably connected with at least one connection duct having at least one chamber to provide for volume compensation e.g. in temperature fluctuations or leakage loss of MRF.

In all the configurations and specific embodiments the damper shaft may be configured as one piece. In preferred configurations the damper shaft is configured in two pieces or three pieces or multiple pieces. Preferably the two, three or more parts can be non-rotatably connected or coupled with one another. In a configuration where a hollow portion of the damper shaft (hollow shaft) accommodates an equalizing device as described above, a junction shaft is preferably provided which is axially connected and non-rotatably coupled with the hollow shaft. The junction shaft and the hollow shaft may preferably be axially screwed to one another.

In all the configurations it is preferred for at least one duct to run from the interior to the housing surface which duct is connected on the inside with at least one chamber and which can be closed at the outwardly end for example by a cover. Then an external equalizing device may be connected from the outside as required. A hollow space that may be present in the interior of the damper shaft may be filled up with an insert.

Preferably the housing is provided with at least one sensor and in particular at least one angle sensor and/or at least one displacement sensor. In preferred configurations an absolute angle sensor or displacement sensor and/or a relative angle sensor or displacement sensor may be provided. Then for example an imprecise absolute sensor always provides an approximate value while following movement, the relative sensor then obtains a precise value which can then be used. Then for example in the case of a switch-off there will always be an "approximately" correct value for first starting controlling.

The housing and in particular an outside surface of the housing is preferably provided with at least one mechanical stopper interacting with the damper shaft and providing an effective rotational angle limiter without having the partition walls go into lockout. This facilitates the mechanical design of the strength of the components.

In all the configurations it is preferred to provide a temperature sensor for capturing the temperature of the magnetorheological fluid. Such a temperature sensor allows to provide for controlling adapted to the presently prevailing temperature so that the rotary damper always shows the same performance independently of the temperature of the magnetorheological fluid.

In all the configurations it is particularly preferred for the damping circuit of the magnetorheological fluid to be disposed completely inside the housing. This allows a particularly simple and compact structure.

Preferably an angle sensor is provided for capturing a measure for an angular position of the damper shaft. This enables angle-dependent damping control. For example increased damping may be set near an end position.

In all the configurations it is preferred to provide a load sensor for capturing a characteristic value of a rotational force on the damper shaft. This then allows load-dependent control for example to optimally utilize the damper travel still available.

In all the configurations it is also preferred that at least one sensor device is comprised including at least one position and/or distance sensor for capturing a position and/or distance from surrounding objects. The control device is preferably configured and set up to control the rotary damper in dependence on the sensor data from the sensor device.

In a preferred specific embodiment the prosthesis device comprises a control device and/or a plurality of in particular interconnected rotary dampers.

In particular a prosthesis device having multiple interlinked rotary dampers allows a great variety of applications. Thus for example in leg prosthesis devices multiple dampers may be used the controls of which are interconnected.

In all the configurations the prosthesis device with the rotary damper has manifold uses. A considerable advantage of the prosthesis device according to the invention consists in the fact that the displacing device is provided with magnetorheological fluid as a working fluid. Thus the magnetic field of the magnetic field source can be controlled and set by a control device in real time, i.e. in a matter of milliseconds (less than 10 or 20 ms) and thus the braking momentum applied on the damper shaft may also be set in real time.

The rotary damper of the prosthesis device comprises a displacing device. The displacing device comprises a damper shaft and rotating displacing components. The rotary motion of the damper shaft can be damped (monitored and controlled). The displacing device contains magnetorheological fluid as a working fluid. At least one control device is associated. Furthermore at least one magnetic field source is provided respectively comprised including at least one electric coil. The magnetic field source can be controlled via the control device and the magnetorheological fluid can be influenced via the magnetic field for setting and adjusting damping of the rotary motion of the damper shaft and thus of the connecting components of the prosthesis device.

Such a prosthesis device is very advantageous. One advantage is that the displacing device is provided with magnetorheological fluid as a working fluid. Thus the magnetic field of the magnetic field source can be controlled and set by a control device in real time, i.e. in a matter of milliseconds (less than 10 or 20 ms) and thus the braking momentum applied on the damper shaft may also be set in real time if the rotary damper is intended to apply a specific braking momentum. The structure of the rotary damper is simple and compact and requires a small number of components so that the prosthesis device is inexpensive in manufacturing.

The structure of the prosthesis device according to the invention with a rotary damper is simple and compact and requires a small number of components so as to provide a prosthesis device inexpensive in manufacturing even in (large-batch) series production. In all the configurations it is possible and preferred for the magnetic field source to comprise at least one (additional) permanent magnet. A permanent magnet allows to generate a controlled static magnetic field for example to generate or provide a base momentum of a specific level. This magnetic field of the permanent magnet may be intentionally boosted or weakened by means of the electric coil of the magnetic field source so that the magnetic field can preferably be set and adjusted as desired between 0 and 100%. This results in a braking momentum which can also preferably be set between 0% and 100%. If the magnetic field is switched off or reduced to a low value, a weak or very weak base momentum of the prosthesis device can be generated.

It is possible and preferred to permanently change the magnetization of the permanent magnet by at least one magnetic pulse of an electric coil. In such a configuration the permanent magnet is influenced by magnetic pulses of the coil so as to permanently change the field strength of the permanent magnet. The permanent magnetization of the permanent magnet may be set by the magnetic pulse of the magnetic field generating device to any desired value between zero and remanence of the permanent magnet. The magnetization polarity can be changed as well. A magnetic pulse for setting the magnetization of the permanent magnet is in particular shorter than 1 minute and preferably shorter than 1 second and particularly preferably the pulse length is less than 10 milliseconds.

The effect of a pulse is that the shape and strength of the magnetic field is maintained permanently in the permanent magnet. The strength and shape of the magnetic field may be changed by at least one magnetic pulse of the magnetic field generating device. A damped magnetic alternating field can demagnetize the permanent magnet.

A material suitable for such a permanent magnet showing changeable magnetization is for example AlNiCo but other materials showing comparable magnetic properties may be used as well. Moreover it is possible to manufacture instead of a permanent magnet the entirety or parts of the magnetic circuit from a steel alloy showing strong residual magnetization (high remanence).

It is possible to generate with the permanent magnet, a permanent static magnetic field which can be superposed by a dynamic magnetic field of the coil for setting the desired field strength. The magnetic field of the coil may be used to change the present value of the field strength as desired. Alternately, two separately controlled coils may be used.

In all the configurations it is preferred for the permanent magnet to consist at least in part of a magnetically hard material whose coercive field strength is above 1 kA/m and in particular above 5 kA/m and preferably above 10 kA/m.

The permanent magnet may at least in part consist of a material showing a coercive field strength of less than 1000 kA/m and preferably less than 500 kA/m and particularly preferably less than 100 kA/m.

In all the configurations it is preferred to provide at least one energy storage device. The energy storage device is in particular rechargeable. The energy storage device is in particular mobile and may be disposed on, or even incorporated in, the prosthesis device or the rotary damper. The energy storage device may for example be configured as an accumulator or a battery.

The rotary damper may also serve to damp rotary motion between two components so as to damp for example rotary motion of a car door or a tailgate of a motor vehicle or a gull-wing door or a hood (bonnet). It may also be employed in a machine to damp its rotary motions.

A prosthesis device according to the invention may be provided e.g. for a hip, a foot or an arm and may comprise at least one rotary joint with a rotary damper. It is also possible to use respectively configure the prosthesis device as an orthosis comprising at least one rotary damper. Orthoses may also be equipped accordingly.

The presently described rotary damper of the prosthesis device may be extremely compact in structure and very inexpensive in manufacture. The magnetic sealing by way of magnetorheological fluid allows to achieve a high-level sealing effect. High maximum pressures of 100 bar and more are achievable.

The force path in the prosthesis device according to the invention may be controlled continuously, variably and very fast by way of the electric current applied to the electric coil.

The prosthesis device may advantageously be linked to a computer or a smartphone to set and adjust the prosthesis device and/or to protocol its operation. Then the ideal settings and adjustments are programmed in the computer or smartphone.

A spring may be integrated in the prosthesis device. The spring may be a torsion spring, coil spring, leaf spring or air/gas spring in functional connection with other parts.

Preferably the two halves are coupled in the zero-current state (e.g. by permanent magnet or remanence in the magnetic field circuit) and they are decoupled as desired by means of electric current.

The features according to the invention allow to achieve high pressure drops even in the case of complex contours and contour transitions, involving little technical work and costs.

Another prosthesis device according to the invention in the shape of e.g. a prosthesis or an orthosis or an exoskeleton comprises a rotary damper and a housing, at least one magnetic field source and a damper volume provided with magnetorheological fluid and subdivided by at least one partition unit connected with a damper shaft into at least two (variable) chambers. Gap sections are formed between the partition unit and the housing. The housing, the magnetic field source and the partition unit are configured and set up for a magnetic field of the magnetic field source to flow through the significant gap sections between the partition unit and the housing.

Preferably at least one partition unit is provided that is connected with the housing. A gap section is in particular configured between the partition unit and the shaft through which the magnetic field of the magnetic field source can flow.

The partition unit connected with the shaft is in particular configured as a swiveling vane.

Advantageously a radial damping gap and two axial sealing gaps are configured between the swiveling vane and the housing.

Preferably at least one magnetic field source with at least one controllable electric coil is comprised. In dependence on the strength of the magnetic field in particular the strength of damping is adjusted.

A method according to the invention for damping movements of a prosthesis device with a rotary damper provides for the rotary damper of the prosthesis device to comprise at least one magnetic field source and a damper volume provided with magnetorheological fluid and subdivided into at least two chambers by at least one partition unit connected with a damper shaft. Gap sections are formed between the partition unit and the housing. A magnetic field of the magnetic field source flows (as required) through the significant gap sections between the partition unit and the housing to influence the damping and in particular to set and adjust the strength of damping.

The magnetic field source comprises at least one controllable electric coil and controls the damping strength by way of the strength of the magnetic field. The controlled magnetic field preferably acts simultaneously in the significant gap sections. This controls not only the damping but it likewise controls the sealing strength, thus changing the base momentum. Thus, the base momentum is considerably lower in the case of weak magnetic field strengths.

Basically, permanent magnets may be attached for sealing gaps in the case of MRF. One permanent magnet or multiple permanent magnets may be employed. Then these act basically as do mechanical (rubber) sealing members. This is also feasible on a pivoting component including in the interior pressure area. This sealing is also feasible for rectangular surfaces. Such a sealing is not or not readily possible with electric coils which must be incorporated virtually "centrally" in the magnetic circuit. Preferably in a pressureless area and with fixed cables and round as a winding part. Attachment is thus much more complicated than in the case of permanent magnets. Particularly if the lowest possible quantity of electric coils is intended to influence more than one gap or all of the gaps. With the present invention the coils are not subjected to pressure and their winding may be normal. In total the construction is very simple and inexpensive in manufacture. Moreover the base momentum varies with the strength of the generated magnetic field. In the case of a very low or absent magnetic field the friction is set very low since the gaps are large.

In all the configurations the swiveling angle can be varied by means of the quantity of partition units or the quantity of vanes. In the case of one partition unit, a swiveling angle of ca. 300 degrees is achieved. Two partition units provide for a swiveling angle of ca. 120 degrees and with four vanes, ca. 40 degrees. The more partition units are provided, the higher is the transmissible momentum.

It is also possible to series-connect, i.e. to cascade, two or more partition units (swiveling vanes). One single partition unit allows a swiveling angle of ca. 300 degrees. Connecting the output shaft with the housing of a second rotary damper enables 600 degrees on the output shaft of the second rotary damper. In applications requiring more than 300 degrees the swiveling angle can thus be increased. Providing suitable nesting the realization will save on mounting space.

The applicant reserves the right to claim protection for a method of manufacturing prosthesis devices wherein firstly at least a two- or three-dimensional scan of at least part of the body of the future user or a representative replica is carried out. The data thus obtained allows to specify the basic shape and size with the option of manual modifications. In particular can a design be selected. Preferably the specified data is transmitted for construction to a manufacturing facility which manufacturing facility may e.g. be, or at least comprise, a 3D printer. Following post-processing if any and/or covering of the body or housing of the prosthesis device proper and mounting the further components and parts (controls, cables, rotary damper components, outer shell) mechanical fitting—if required—to the user's body may be carried out.

Manufacturing may be outsourced e.g. to a service provider such as a craftworkshop or other suppliers.

Basically this is an e.g. linear work process wherein each junction point is represented by a service provider or an industrial enterprise or some service. In the future the entire process may be facilitated by way of interconnecting the process steps involved. Thus, any or all may join to establish a service provider or to outsource specific services. These outsourced services may be offered e.g. by universities or medical facilities, sports facilities, by military veterans or rehabilitation facilities. A service provider having a 3D printer may be involved.

Alternative options may be provided for individual process steps. An alternative concerning 3D print may e.g. be an enterprise supplying the prostheses, or the prosthesis body is manufactured by CNC or machined or made manually e.g. of wood or other suitable materials or it may e.g. be carved.

The design process step may employ a program or an "App" which operates (or replaces) a standard CAD program by inputting (or transmitting) specific parameters. This means that body data is imported or input. In a menu e.g. the body weight may be input or selected. Specific design models and/or technical parameters may be selected from an existing library. For example specific magnetorheological modules (MRF module) may also be selectable.

It is also possible for a program or the program to offer a suitable (body) structure.

A service provider may also e.g. offer trainings or carry out installation.

Optionally the customer may input certain general parameters in his computer or input specific data in his smartphone, or select a mode or features.

It is possible to provide a prosthesis device primarily for "damping" only, in particular if no spring or just a small spring is provided for pre-stressing and (abruptly) releasing. Alternately a spring may be integrated. A modular system may be provided. Damping and optionally springing is feasible in the rebound stage and the compression stage.

Further advantages and features of the present invention can be taken from the description of the exemplary embodiments which will be discussed below with reference to the enclosed figures.

BRIEF DESCRIPTION OF THE SEVERAL VIEWS OF THE DRAWING

FIG. 8 a section of another rotary damper for a prosthesis device;

FIG. 9 a section along the line B-B in FIG. 8;

FIG. 10 an enlarged detail of FIG. 9;

DESCRIPTION OF THE INVENTION

Figure 1:
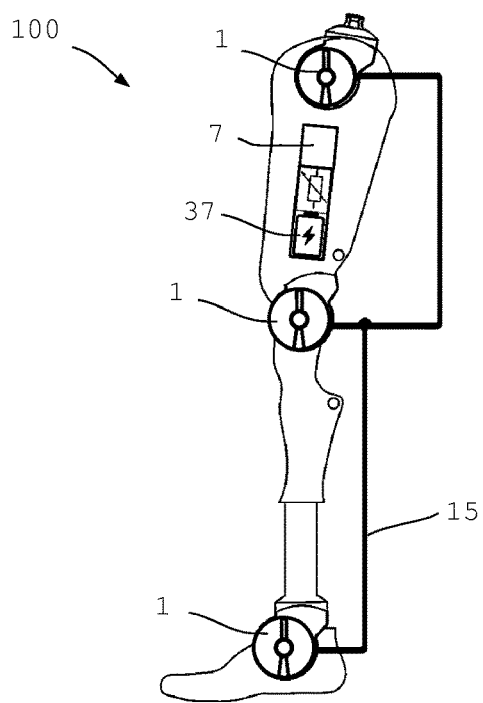
FIG. 1 a first prosthesis device according to the invention having multiple rotary dampers.

FIG. 1 shows a prosthesis device 100 according to the invention which in this case is a leg prosthesis 100 and comprises one or more rotary damper(s) 1. The leg prosthesis 100 according to the invention comprises three rotary dampers 1 configured functionally similar or identical, provided with one rotary damper 1 at the hip joint, another rotary damper 1 at the knee joint, and a third rotary damper 1 at the ankle joint. The rotary dampers 1 are interconnected through fluid lines 15 and also electrically coupled with one another so as to enable interlinked controlling of the prosthesis device 100. A control device 7 and an energy storage device 37 are also incorporated in the prosthesis device 100. The rotary dampers 1 are designed for pivoting motions up to approximately 180° respectively up to 90° in the case of the rotary damper 1 for the knee joint and for the ankle joint.

Figure 2:
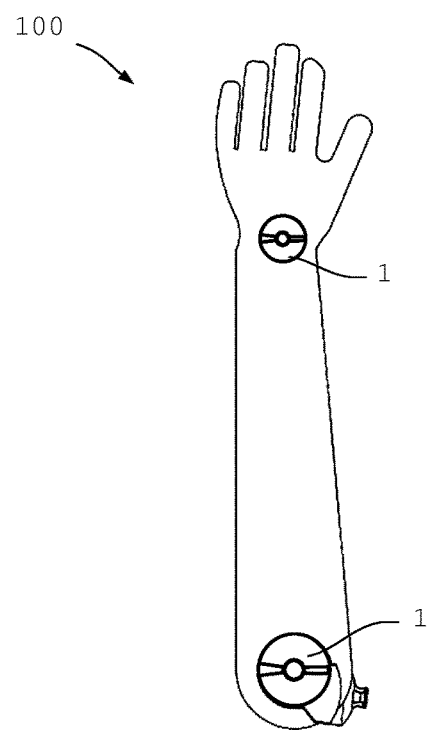
FIG. 2 a second prosthesis device according to the invention.

FIG. 2 shows use in a prosthesis device 100 configured as a forearm prosthesis wherein again, two interlinked rotary dampers 1 are used, one at the elbow joint and one in the wrist.

Figure 3:
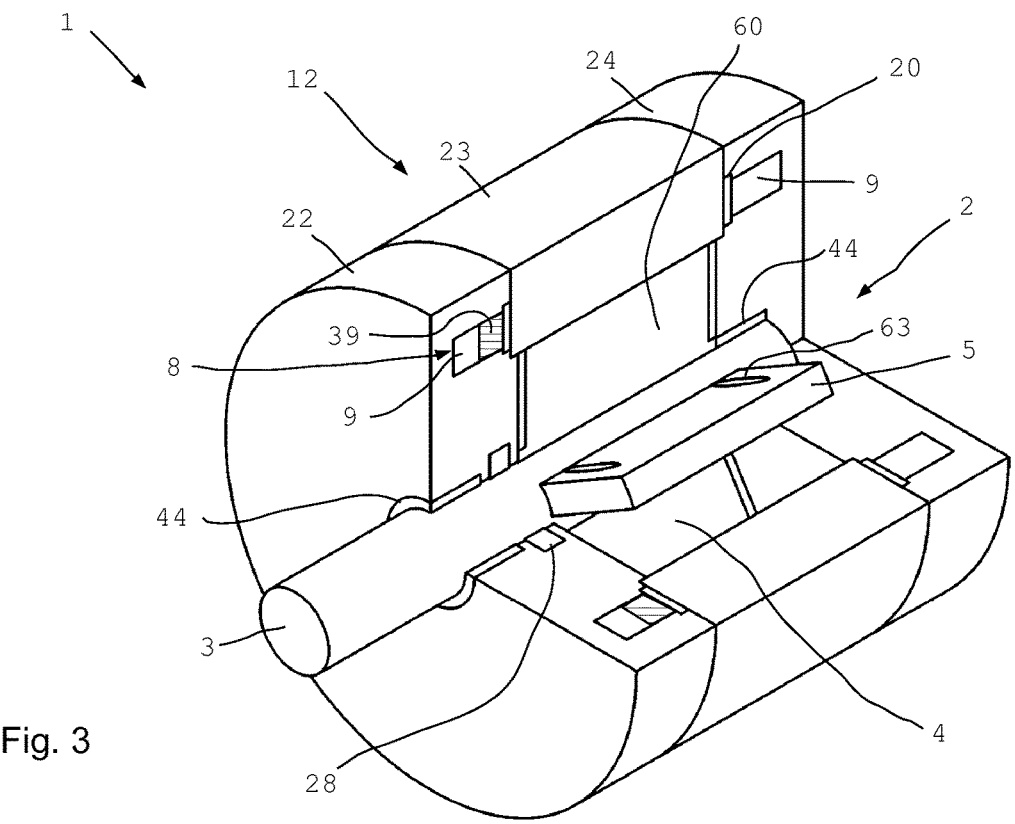
FIG. 3 a sectional detail view of a rotary damper of the prosthesis device according to FIG. 1.

FIG. 3 shows a sectional detail view of the rotary damper of the prosthesis device 100 e.g. of FIG. 1. The rotary damper 1 of the prosthesis device 100 has a housing 12 and a damper shaft 3 configured pivotable relative to one another. The damper shaft 3 is rotatably supported in the housing 12 by means of sliding bearings 44. This housing 12 consists of three sections or housing parts, a first end part 22 and a second end part 24 at the other end and in-between, a center part 23. Each of the parts respectively each of the regions is a separate component which are connected with one another during mounting. Alternately it is possible for the three housing part sections or regions to be parts of one single or two components.

The two end parts 22 and 24 accommodate a circumferential electric coil 9 each, which serve to generate the magnetic field required for damping. The internal space of the rotary damper 1 provides a damper volume 60. A displacing device 2 comprising partition units 4 and 5 is configured in the housing. The partition units 4 and 5 partition the damper volume 60 into two or more chambers 61 and 62. The partition unit 4 is configured as a partition wall and fixedly connected with the housing 12. The partition unit 5 is likewise configured as a partition wall or a swiveling vane and is fixedly connected with the damper shaft 3. Preferably the partition unit 5 is formed integrally with the damper shaft 3. The damper volume 60 is presently filled with magnetorheological fluid. The damper volume 60 is sealed outwardly by means of a seal 28 in the housing part 22. If a pivoting motion occurs, the partition units 4 and 5 displace the magnetorheological fluid (MRF) contained in the damper volume so that the MRF partially flows from the one into the other chamber.

The magnetic field source 8 in the housing part 22 consists of electric coils 9 and may furthermore comprise at least one permanent magnet 39 each being annular in configuration and accommodated in the housing part 22. In this exemplary embodiment the two end parts are provided with electric coils 9 and optionally also with permanent magnets 39. The permanent magnet 39 specifies a specific magnetic field strength which may be modulated through the electric coil 9 and can thus be neutralized or boosted.

Two partition units 4 protrude radially inwardly from the housing into the damper volume 60. The partition units 4 form partition walls and thus delimit the feasible rotary motion of the damper shaft 3 on which two partition units 5 are also configured which protrude radially outwardly from the damper shaft. Rotating the damper shaft 3 swivels the partition walls 5 which thus form swiveling vanes.

The electric coils 9 in this exemplary embodiment are disposed radially relatively far outwardly and are axially inwardly delimited by a ring 20 that is magnetically non-conductive or poorly conductive and serves to form the magnetic field curve. The ring 20 has a hollow cylindrical shape.

These partition units 5 show connection ducts 63 which will be described in more detail in the discussion of FIGS. 5 and 14.

Figure 4:
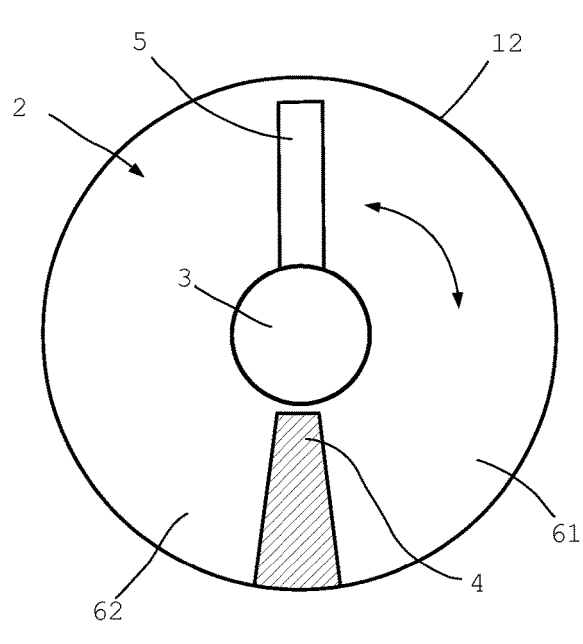
FIG. 4 a schematic section of a rotary damper for a prosthesis device according to the invention.

FIG. 4 shows a cross-section of a simply structured rotary damper 1 of a prosthesis device 100. The displacing device comprises just one (single) partition unit 4 which extends radially inwardly from the housing into the damper volume 60. The interior of the housing rotatably accommodates the damper shaft 3 from which again only one partition unit 5 extends radially outwardly. The partition units 4 and 5 of the displacing device 2 serving as partition walls variably subdivide the damper volume 60 into two chambers 61 and 62. As the damper shaft rotates in the clockwise direction the volume of the chamber 61 is reduced and the volume of the chamber 62 is enlarged while a reversed rotary motion causes the volume of the chamber 61 to enlarge correspondingly.

Figure 5:
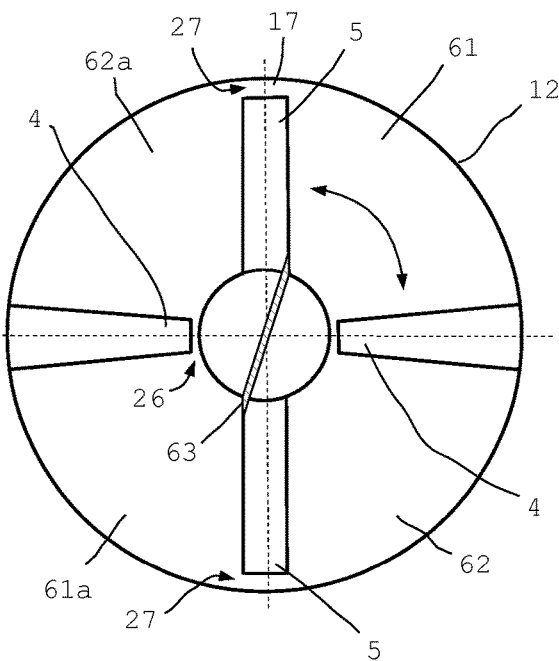
FIG. 5 a section of another rotary damper for a prosthesis device according to the invention.

FIG. 5 shows a cross-section of another exemplary embodiment with two partition units each attached to the housing and the damper shaft 3. The partition units 4 and 5 disposed symmetrically thus enable a swiveling motion of the damper shaft 3 by nearly 180°. Between the partition units 4 and 5, two chambers 61 and 61a, and 62 and 62a respectively are formed. As the damper shaft 3 is rotated clockwise, the chambers 61 and 61a form the high pressure chambers while the chambers 62 and 62a are then low pressure chambers.

To cause pressure compensation between the two high pressure chambers 61 and 61a, suitable connection ducts 63 are provided between the chambers 61 and 61a, and 62 and 62a.

Between the radially outwardly end of the partition units 5 and the inner periphery of the basically cylindrical damper volume 60, a radial gap 27 is formed which serves as a damping duct 17. Moreover, radial gaps 26 are configured between the radially inwardly end of the partition units 4 and the damper shaft 3. The gaps 26 are dimensioned so as to enable smooth rotatability of the damper shaft 3 and to reliably prevent the magnetorheological particles from jamming in the magnetorheological fluid inside the damper volume 60 near the gaps 26. To this end the gap 26 must show a gap height that is at least larger than the largest diameter of the particles in the magnetorheological fluid.

Such a large gap 26 of a size of approximately 10 μm to 30 μm would usually cause a considerable leakage flow through the gap 26. This would effectively prevent high pressure build-up in the chambers 61 respectively 62. According to the invention this is prevented in that a magnetic field is likewise applied on the gap 26 so that the gap 26 is magnetorheologically sealed, at least when a braking momentum is to be applied. This causes reliable sealing so as to largely prohibit pressure loss.

Figure 6:
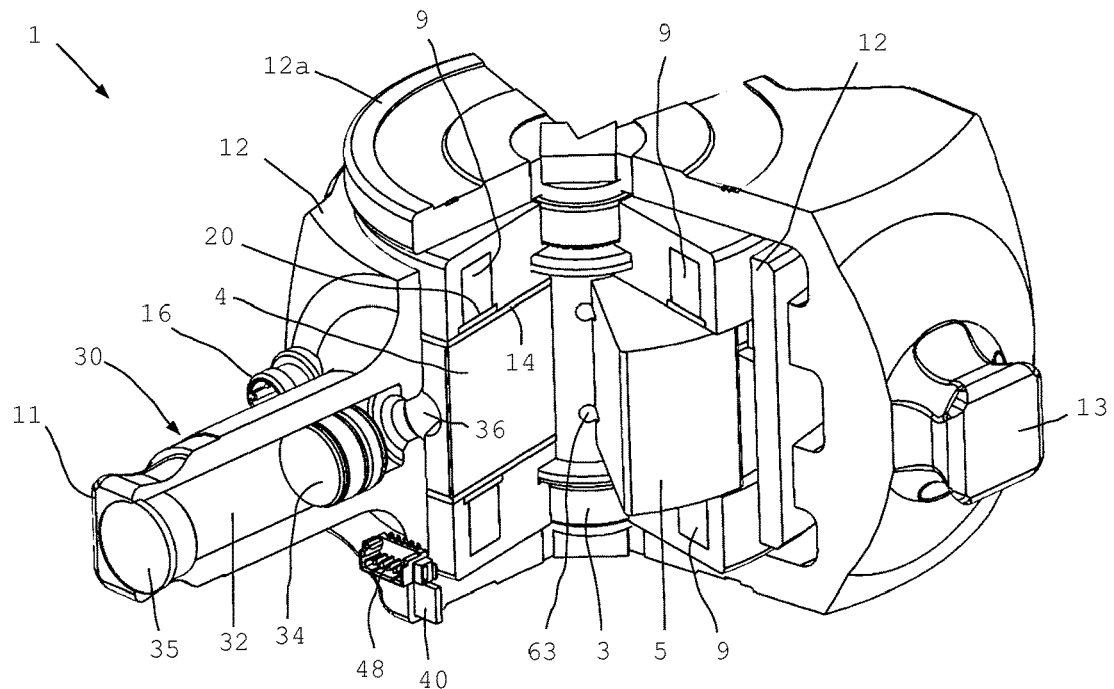
FIG. 6 a sectional detail view of a rotary damper of a prosthesis device.

FIG. 6 shows another exemplary embodiment of a prosthesis device according to the invention with a rotary damper 1. The rotary damper 1 has a damper shaft 3 rotatably supported in a housing 12. The damper shaft 3 or the housing respectively are connected with junctions 11 and 13 pivotal relative to one another.

The damper volume 60 is subdivided into chambers 61 and 62 by partition units 4 and 5 as is the case in the exemplary embodiment according to FIG. 5.

Again the housing 12 consists of three housing sections or housing parts, the axially outwardly housing parts receiving one electric coil 9 each for generating the required magnetic field.

A power connection 16 supplies the rotary damper 1 with electric energy. A sensor device 40 serves to capture the angular position. Moreover, the sensor device can capture a measure of the temperature of the magnetorheological fluid. The signals are transmitted through the sensor line 48.

The partition unit 4 is accommodated stationary in the housing 12 and is preferably inserted into, and fixedly connected with, the housing during mounting. To prevent magnetic short circuit in the regions of the partition unit 4, an insulator 14 is preferably provided between the partition unit 4 and the housing parts 22 respectively 24.

FIG. 6 shows the equalizing device 30 which comprises an air chamber 32 that is outwardly closed by a cap 35. The air chamber 32 is followed inwardly by the dividing piston 34 which separates the air chamber 32 from the equalizing volume 29. The equalizing volume 29 is filled with magnetorheological fluid, providing compensation in temperature fluctuations. Moreover the equalizing volume 29 serves as a reservoir for leakage loss occurring during operation.

Figure 7:
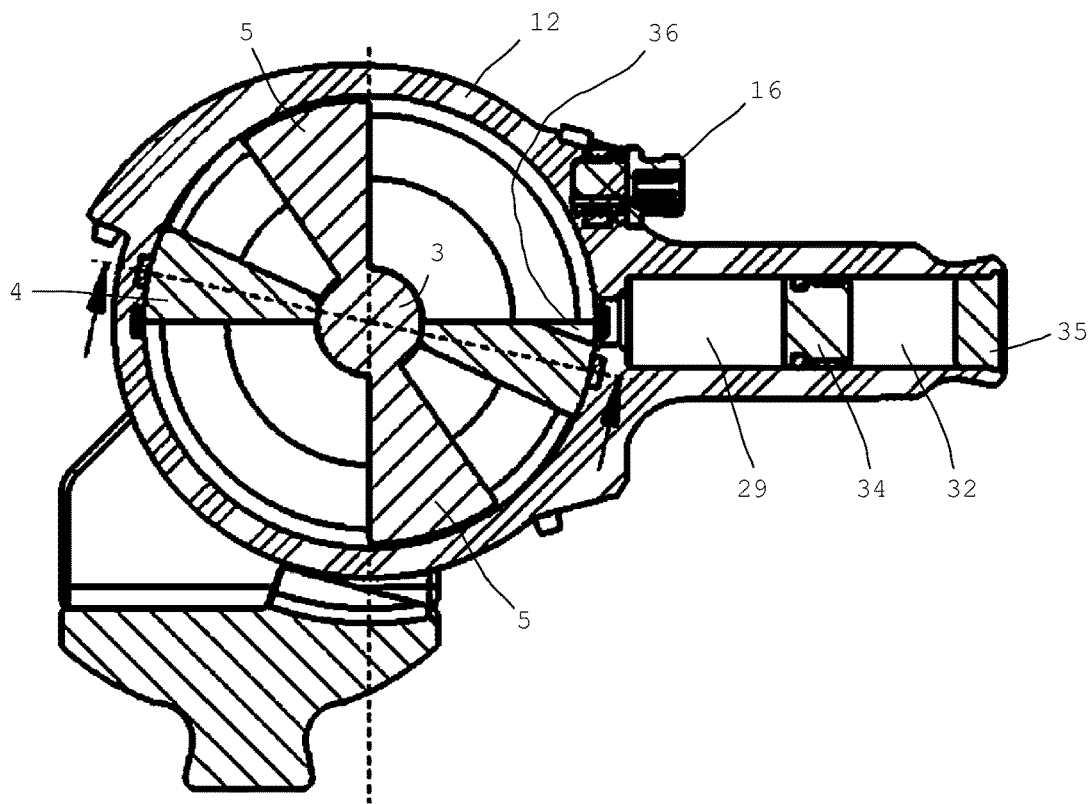
FIG. 7 a section of the rotary damper of FIG. 6.

FIG. 7 shows a cross-section of the rotary damper of the prosthesis device according to FIG. 6 wherein one can recognize that pairs of opposite partition units 4 and 5 are disposed in the housing respectively attached to the damper shaft 3. Between each of the partition units 4 and 5, chambers 61 and 61a respectively 62 and 62a are formed in the damper volume 60. The insertion of pairs of partition units 4 and 5 allows to double the active rotational force. The equalizing volume 29 is connected through a duct 36.

The duct 36 is guided into the damper volume 60 on the edge of the partition unit 4 so that even in the case of a maximal pivoting motion between the damper shaft 3 and the housing 12 a connection with the equalizing volume 29 is provided. In this configuration the equalizing volume must be prestressed to beneath the maximum operating pressure by applying suitable pressure on the air chamber 32. The prestress may also be applied by a mechanical element such as a coil spring.

FIG. 8 shows a cross-section of a rotary damper 1 of another exemplary embodiment of a prosthesis device 100 according to the invention. The rotary damper 1 in turn is provided with pairs of partition units 4 and 5, each of which is connected with the housing or the damper shaft 3 respectively. Again, two electric coils are provided which are invisible in the illustration of FIG. 8 because they are respectively disposed in front of and behind the sectional plane.

Between the inner housing wall and the radially outwardly end of the partition elements 5 a radially outwardly gap 27 is formed on which a suitable magnetic field is applied for damping. A gap 26 is formed radially inwardly between each of the inner ends of the partition elements 4 and the damper shaft 3 which is sealed by way of a magnetic field.

Unlike in the preceding exemplary embodiment the equalizing volume is connected centrally. The equalizing volume 29 is connected with the interior of a partition unit 4 via the duct 36.

FIG. 9 shows the cross-section E-E of FIG. 8, and FIG. 10 shows an enlarged detail of FIG. 9. The duct 36 is schematically drawn in FIG. 10 and is connected with a duct in which a valve unit 31 is disposed which is presently a double-acting valve unit. The valve unit 31 comprises two valve heads 31a at the opposite ends of the duct. Seals 33 serve for sealing when the pertaining valve head 31 is disposed in its valve seat. The duct 36 opens into an intermediate region.

On the side where the higher pressure is prevailing the valve head 31 of the valve unit 31 is pressed into the pertaining valve seat. On the other side this makes the valve head 31a lift off the valve seat and allows a free flow connection to the duct 36 and thus to the equalizing volume 29. This enables the compensation of temperature fluctuations. Moreover, if leakage loss occurs, magnetorheological fluid is transferred out of the equalizing volume into the damper volume.

An advantage of this construction is that the equalizing volume only requires a relatively low prestressing pressure of 2, 3 or 4 or 5 bar since the equalizing volume is always connected with the low pressure side and not with the high pressure side of the rotary damper. This configuration reduces the loads and stresses on the seals and increases long-term stability. If the equalizing volume is connected with the high pressure side, a prestressing pressure of 100 bar and more may be useful.

Figure 11:
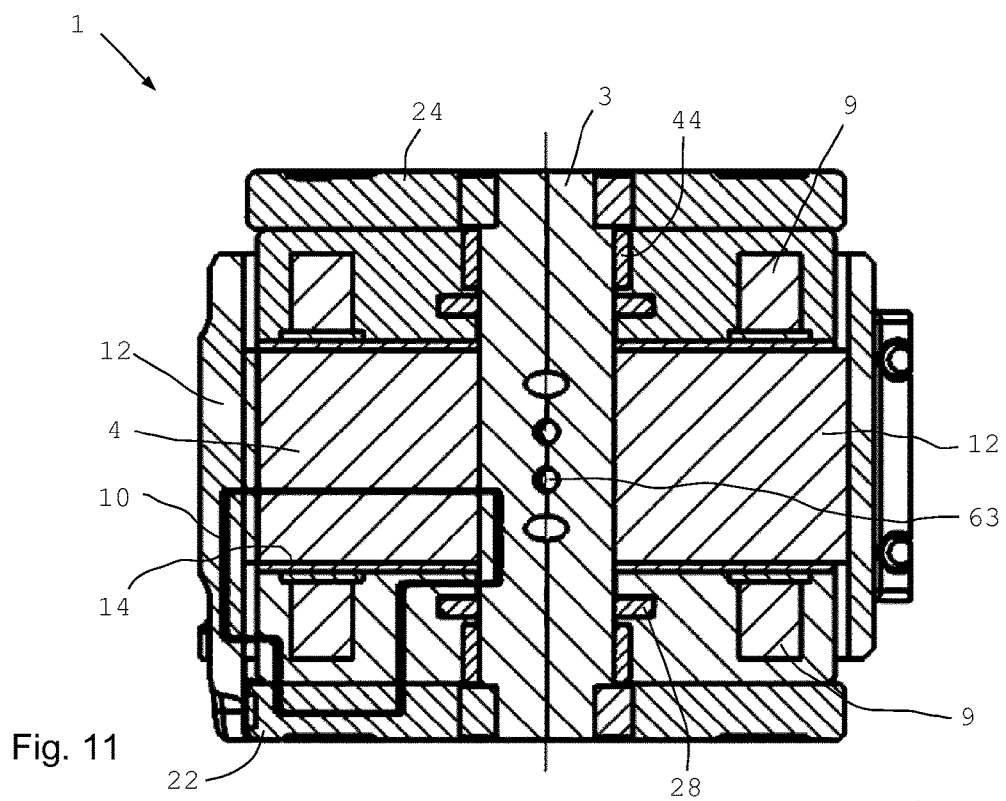
FIG. 11 a cross-section of a rotary damper of a prosthesis device according to the invention with the magnetic field curve inserted.
Figure 12:
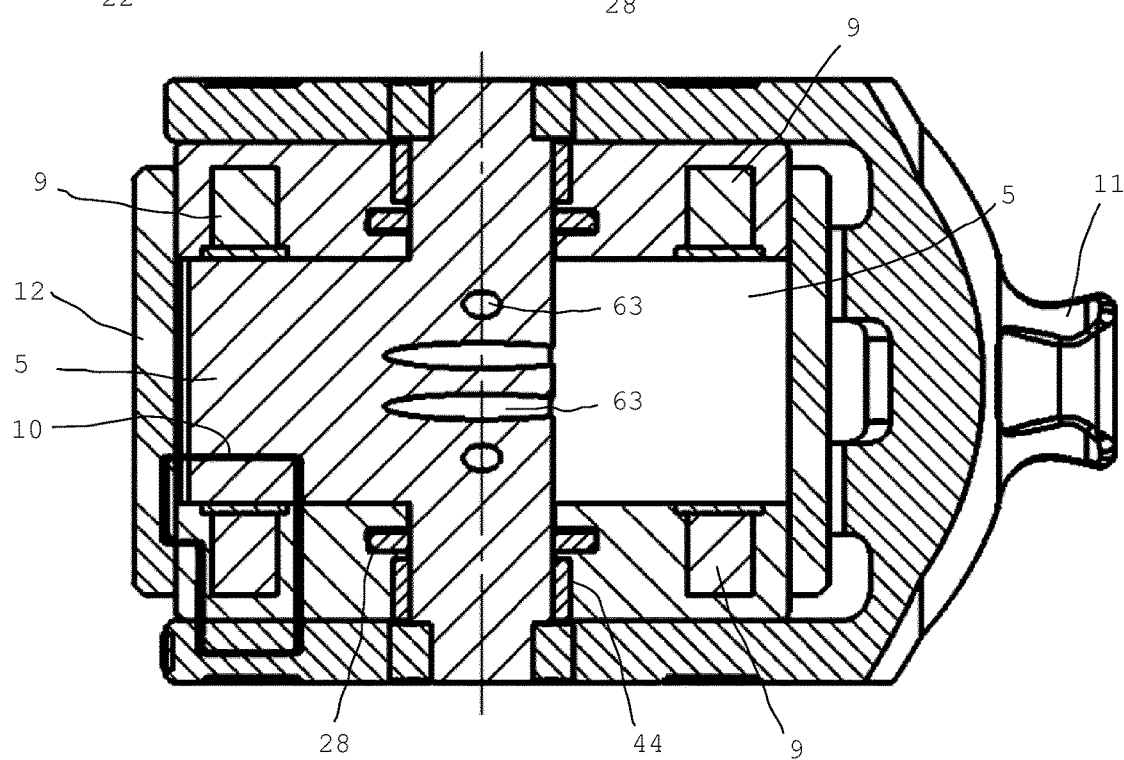
FIG. 12 another cross-section of the rotary damper of FIG. 11 with the magnetic field curve inserted.

FIGS. 11 and 12 show cross-sections of the rotary damper 1 of the prosthesis device 100 illustrating different cross-sections. FIG. 11 shows a cross-section illustrating the partition units 4 connected with the housing in section. The magnetic insulator between the housing side parts 22 and 24 and the partition wall 4 causes the inserted curve of the magnetic field line. The magnetic field lines pass through the radially inwardly gap 26 between the inner end of the partition units 4 and the damper shaft 3 where they thus reliably seal the gap. When the magnetic field is switched off, the damping is reduced, and a weak base friction results.

In the section according to FIG. 11 one can also recognize the sliding bearings 44 for supporting the pivot shaft and the seals 28 for sealing the interior.

FIG. 12 shows a cross-section of a rotary damper 1 of a prosthesis device 100, wherein the section passes through the damper shaft 3 and a partition unit 5 connected therewith. The other of the partition units 5 connected with the damper shaft 3 on the opposite side is shown not in section. FIG. 12 also exemplarily shows the curve of a magnetic field line. It becomes clear that the axial gaps 25 between the partition unit 5 and the housing parts 22 and 24 are sealed by the magnetic field. Furthermore, the radial gap 27 between a radially outwardly end of the partition unit 5 and the housing is also exposed to the magnetic field so that the magnetorheological particles interlink, sealing the gap.

Figure 13:
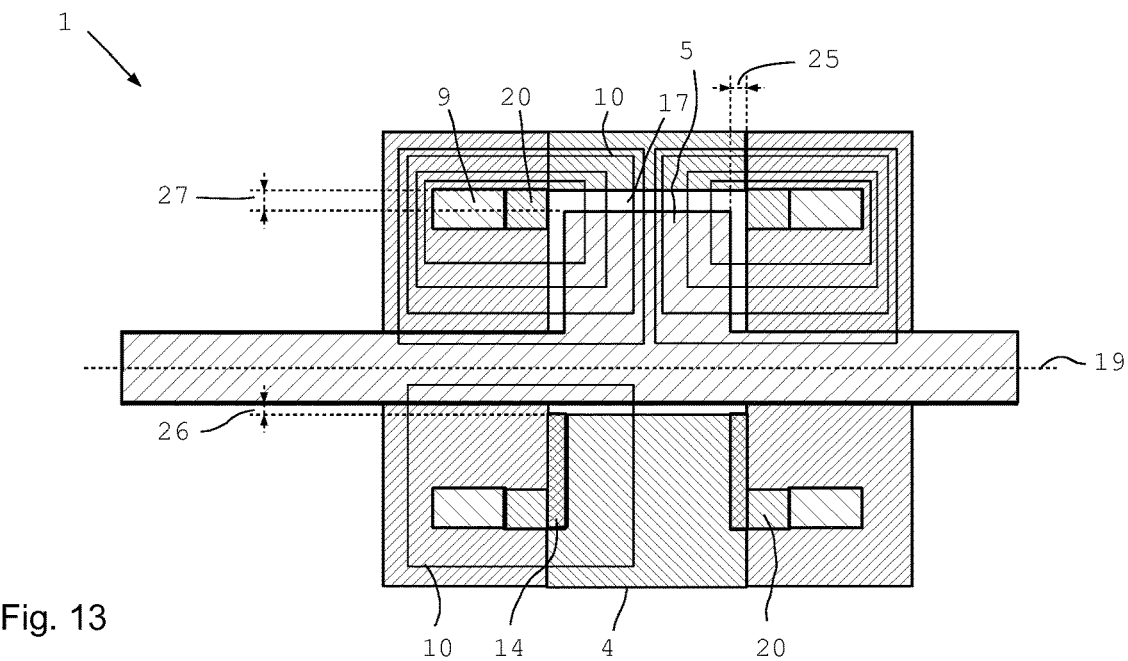
FIG. 13 a schematic cross-section of a rotary damper of a prosthesis device according to the invention.

FIG. 13 shows another schematic cross-section not to scale of a damper device 1 wherein the top half shows a section of the damper shaft 3 and the partition unit 5 connected therewith while the bottom half shows a section of the partition unit 4 connected with the housing. Magnetic field lines are exemplarily drawn. Between the partition unit 4 and the damper shaft there is a narrow gap 26 preferably showing a gap height between approximately 10 and 50 μm. In the axial direction the partition unit 4 lies closely against the lateral housing parts. Between the partition unit 5 and the housing 12 there is a radial gap 27, and on the two axial front faces, an axial gap 25 each.

As a rule the axial gaps 25 show a considerably lower gap height than does the radial gap 27. The gap width of the axial gaps 25 is preferably like the gap width of the radial gaps 26 and is preferably between approximately 10 and 30 μm. The radial gap width 27 is preferably considerably larger and preferably lies between approximately 200 μm and 2 mm and particularly preferably between approximately 500 μm and 1 mm.

As the damper shaft 3 swivels, the volume of a chamber decreases and that of the other chamber increases. The magnetorheological fluid must substantially pass through the gap 27 from the one into the other chamber. This gap 27 serves as a damping duct 17. As can be clearly seen in FIG. 13, the magnetic field lines pass through the damping duct 17 so as to allow to generate a variable flow resistance therein.

The axial gaps 25 are likewise sealed by the magnetic field, at any rate when its magnetic field is made strong enough so that it is no longer guided through the damper shaft 3 alone. It has been found that with increasing strength of the magnetic field the entire magnetic field is no longer guided through the damper shaft 3 but it also passes axially through the axial gap 25 and thus, with increasing strength, seals the entire axial gap 25. A suitable field strength seals accordingly.

As has been described above, in this case the magnetically non-conductive rings 20 serve to prevent a magnetic short circuit at the electric coil 9.

Figure 14:
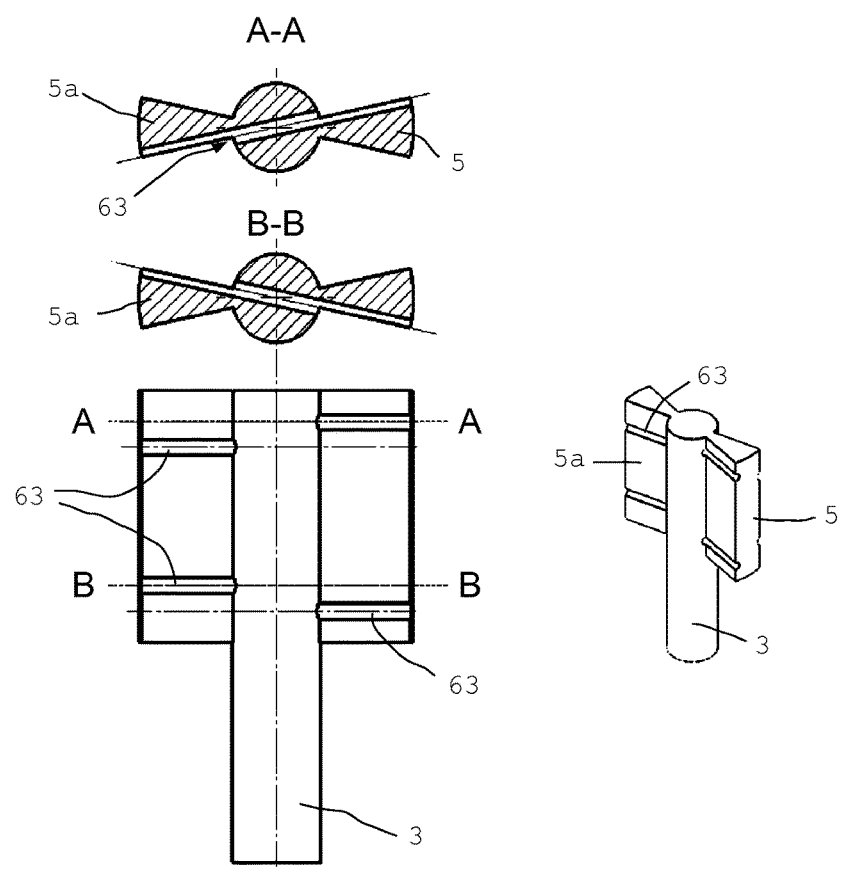
FIG. 14 different views of a damper shaft for a prosthesis device.

FIG. 14 shows different views of the damper shafts 3 equipped with two partition units, the partition units 5 and 5a being diagonally opposed so as to show a symmetric structure. FIG. 14 shows the two connection ducts 63 each interconnecting two opposite chambers 61 and 61a respectively 62 and 62a. To enable pressure compensation between the two high pressure chambers and the two low pressure chambers, while pressure exchange or fluid exchange of a high pressure chamber and a low pressure chamber is only possible through the damping duct 17.

Figure 15:
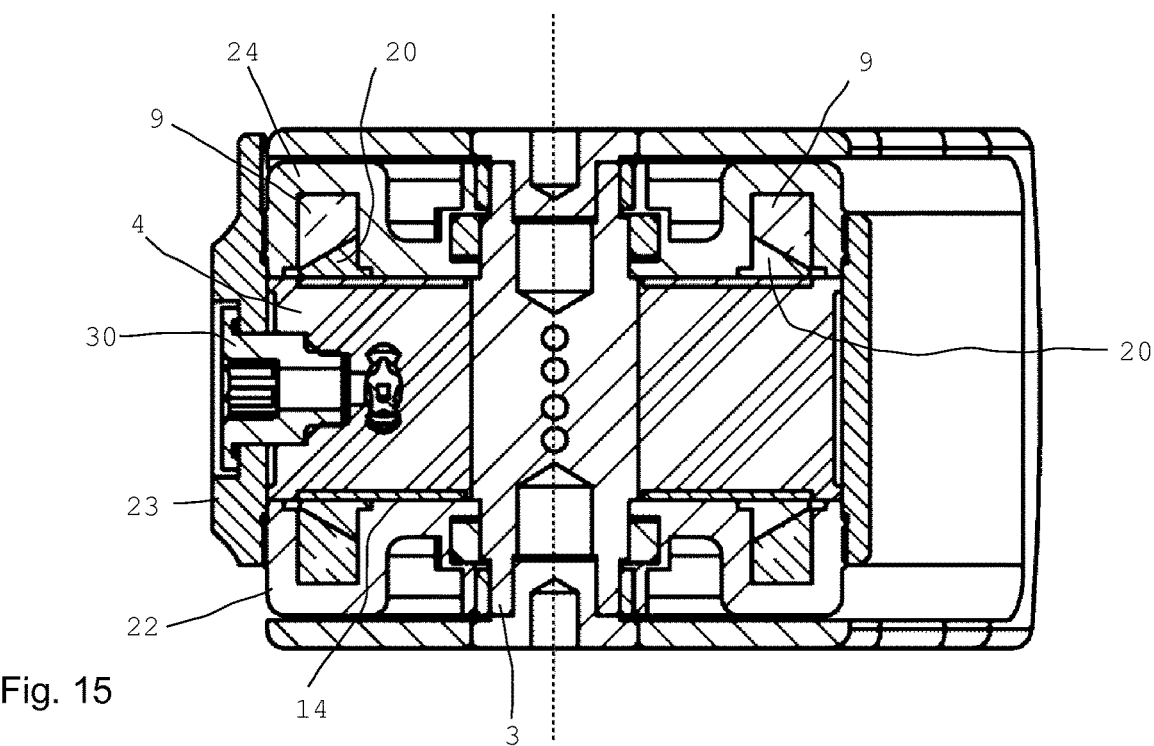
FIG. 15 a section of yet another rotary damper of a prosthesis device.

FIG. 15 shows a cross-section of a rotary damper 1 of another prosthesis device. This rotary damper is particularly small in structure so as to enable a small structured and lightweight prosthesis device. The rotary damper 1 of FIG. 15 may be employed in all the exemplary embodiments and its structure is basically the same. The partition units 4 connected with the housing can be seen in section. The magnetic insulator 14 between the housing side parts 22 and 24 and the partition wall 4 causes a curve of the magnetic field lines similar to FIG. 11. When the magnetic field is switched off, the damping is again reduced and a weak base friction results. The ring 20 is configured magnetically conductive to ensure safe sealing of the lateral axial gaps 26 in the region of the partition element 5. Sealing is safely obtained if a sufficient magnetic field strength is present. Again, as in FIG. 11, the sliding bearings 44 for supporting the swiveling shaft and the seals 28 for sealing the interior can be recognized.

The electric coils 9 are radially arranged in the region of the damper volume. In the region of the swiveling vane the frusto-conical shape of the rings 20 provided with a hollow cylinder leads to a secure sealing also of the lateral axial gaps 26. The rings 20 presently consisting of a magnetically conductive material cause reliable sealing of the axial sealing gaps 26 in the region of the swiveling vane respectively partition elements 5.

Figure 16:
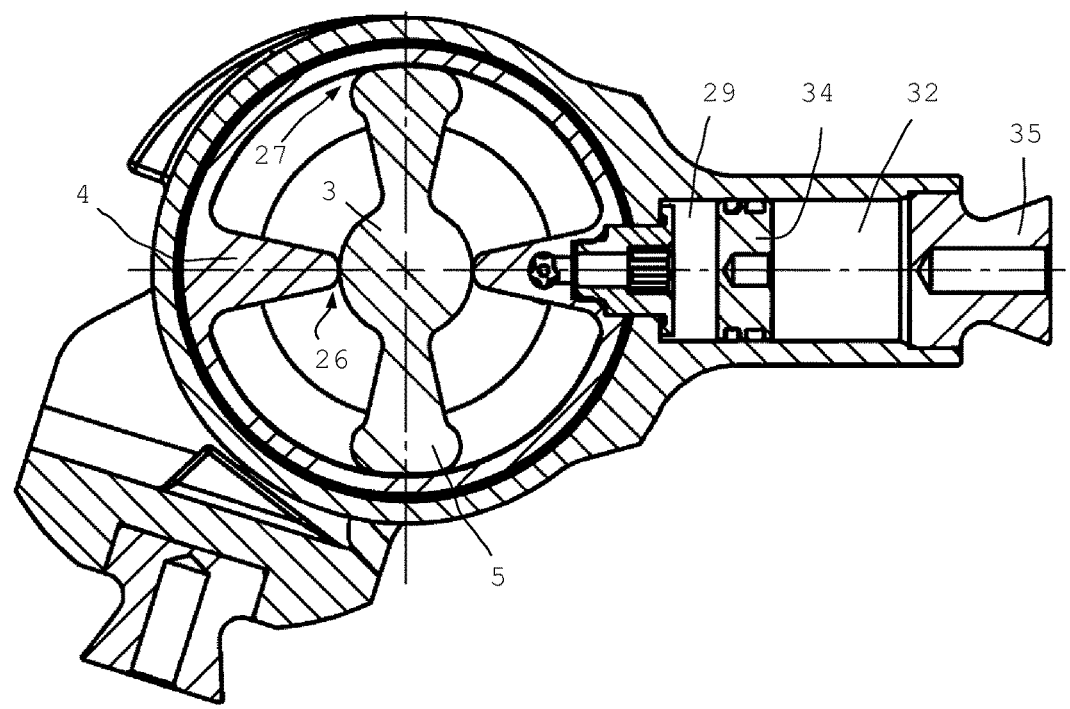
FIG. 16 a schematic cross-section of another rotary damper of a prosthesis device according to the invention.

FIG. 16 shows a variant similar to FIG. 7, wherein again, two partition units each are attached to the housing and the damper shaft 3. The partition units 4 and 5 disposed symmetrically thus enable a swiveling motion of the damper shaft 3 by almost 180°. Between each of the partition units 4 and 5 two high pressure chambers and two low pressure chambers each are formed. The partition units 4 and 5 are configured rounded and flow-optimized so as to prevent flow separation and thus prevent undesirable sediments from the magnetorheological fluid. An equalizing device 30 comprising an equalizing volume 29 is also provided.

Figure 17:
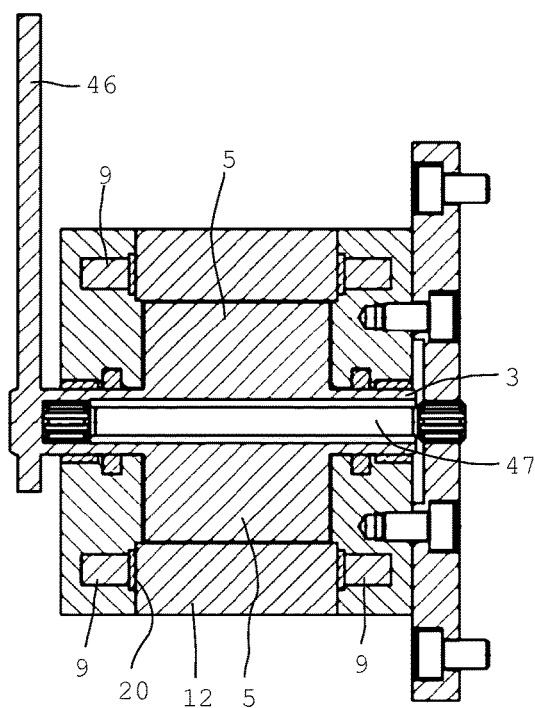
FIG. 17 a prosthesis device with a rotary damper including a torsion bar.

FIG. 17 finally shows another exemplary embodiment wherein the rotary damper 1 of the prosthesis device 100 is additionally equipped with a spring in the shape of a torsion bar. The damper shaft is coupled with one side and the housing, with the other side so that relative motion or relative rotation of the components relative to one another can be controlled to be damped via the rotary damper 1. The components may be adjustable and also provided for complete decoupling. This provides an active prosthesis device which may be set and adjusted for different conditions.

Furthermore, the damper shaft 3 in FIG. 17 is hollow. The spring in the shape for example of a torsion bar is disposed in the interior of the damper shaft so as to enable resetting by way of the spring force of the spring 47.

Figure 18:
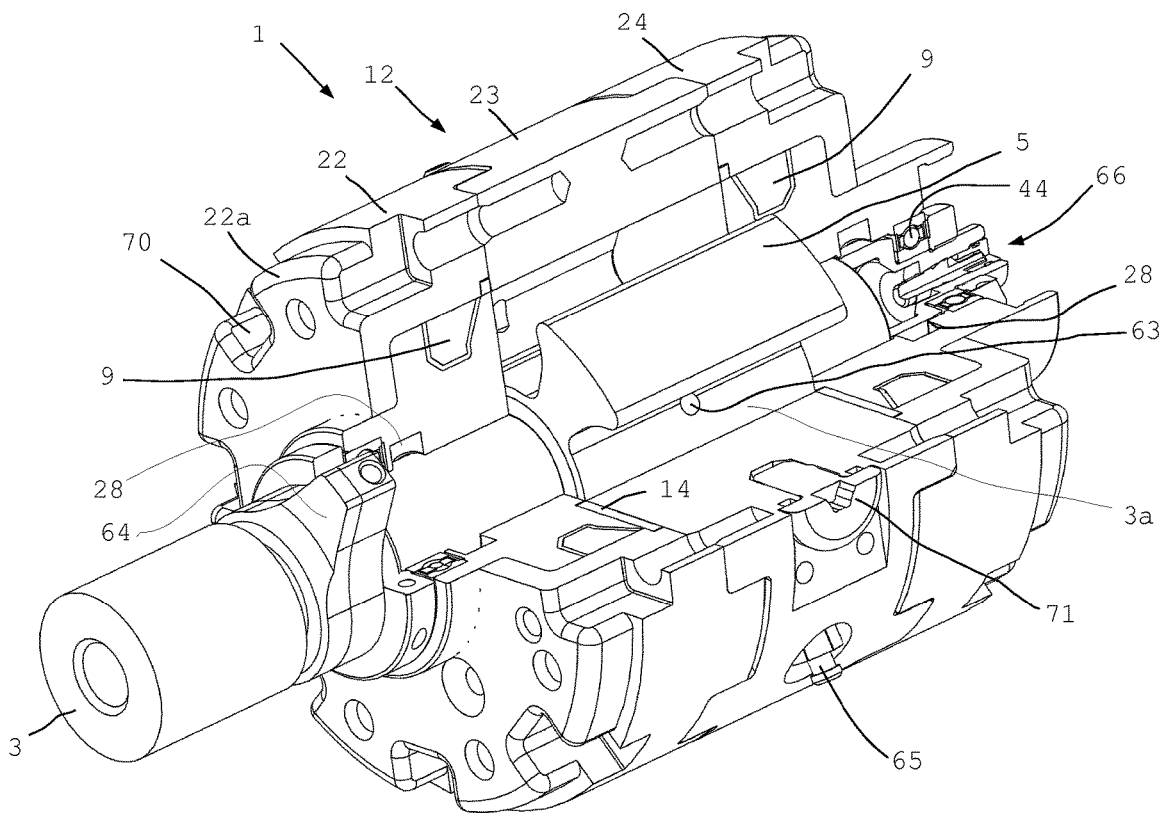
FIG. 18 a sectional detail view of a rotary damper of another prosthesis device according to the invention.

FIG. 18 shows a sectional detail view of another prosthesis device 100 wherein the rotary damper 1 operates basically the same as does e.g. the rotary damper of the prosthesis device 100 according to FIG. 3. Therefore, to the extent possible the same reference numerals are used, and the foregoing description applies identically also to the prosthesis device 100 respectively the pertaining rotary damper 1 of the FIGS. 18-20, unless the description is contrary or supplementary or the drawings show something different. FIG. 21 shows a variant of the rotary damper 1 of the prosthesis device 100 according to FIG. 18.

The rotary damper 1 for a prosthesis device 100 or an exoskeleton of FIG. 18 is likewise provided with a housing 12 and a damper shaft 3 which are configured pivotable relative to one another. The damper shaft 3 is rotatably supported in the housing 12 by means of roller bearings 44. The damper shaft 3 in its entirety is configured in three parts as will be discussed with reference to FIG. 20.

The housing 12 comprises a first end part 22 and a second end part 24 at the other end thereof, and disposed in-between, a center part 23. Both ends also accommodate external housing parts 12a with screwing apertures. The radially outwardly housing part 12a shows a non-round coupling contour 70 with recesses in the region of the end of the reference numeral line. Multiple recesses distributed over the circumference form the non-round coupling contour which allows non-rotatable connection with further components of a hip, knee, ankle, elbow, or e.g. shoulder prosthesis.

The two end parts 22 and 24 accommodate a circumferential electric coil 9 each, which serve to generate the magnetic field required for damping.

As in all the exemplary embodiments, the magnetic field is controllable. As in all the exemplary embodiments and configurations, a stronger magnetic field generates stronger damping (braking action). Simultaneously the stronger magnetic field also achieves better sealing of the gaps 25, 26 and 27 (see the schematic diagram of FIG. 13). Reversely, all the exemplary embodiments and configurations provide for setting and adjusting weaker damping (braking action) by way of a weaker magnetic field. Concurrently the sealing effect at the gaps 25 to 27 is weaker with a weaker magnetic field. This results in a lower base momentum acting without a magnetic field. The sealing effect of the gaps 25 to 27 is low without a magnetic field. This allows to provide a wide setting range as it is not possible in the prior art. The ratio of the maximal rotational force (or maximal braking action) to the minimal rotational force (or minimal braking action) within the provided swiveling angle or within the working area is very large and larger than in the prior art.

In conventional rotary dampers of prostheses, however, the minimal rotational force is already high if a high maximal rotational force is to be generated. The reason is that the seals of the gaps must be configured so as to ensure reliable or at least sufficient sealing including in the case of high active pressures. Reversely, in rotary dampers of prostheses intended to have a low braking momentum in idling, just a weak maximal rotational force is achieved since the seals are configured so as to produce low friction. In the case of high effective pressures this causes considerable leakage flow which strongly delimits the maximally possible rotational force.

The internal space of the rotary damper 1 provides a damper volume. A displacing device 2 comprising partition units 4 and 5 is configured in the housing. The partition units 4 and 5 partition the damper volume 60 into two or more chambers 61 and 62. The partition unit 4 is configured as a partition wall and fixedly connected with the housing 12. The partition unit 5 is likewise configured as a partition wall or a swiveling vane and is fixedly connected with the damper shaft 3. Preferably the partition unit 5 is formed integrally with the damper shaft 3. The damper volume 60 is presently filled with magnetorheological fluid 6. The damper volume 60 is sealed outwardly by means of a seal 28 in the housing part 22. If a pivoting motion occurs, the partition units 4 and 5 displace the magnetorheological fluid (MRF) contained in the damper volume so that the MRF partially flows from the one into the other chamber. A connection duct or equalizing duct 63 serves for pressure compensation between the chambers 61 and 61a. A suitable second connection duct 63a (see FIG. 20) serves for pressure compensation between the chambers 62 and 62a.

The rearwardly end in FIG. 18 also shows a valve 66 through which compressible fluid is filled into the equalizing device 30. Nitrogen is in particular used. The valve 66 may for example be incorporated in a screwed-in top or cap.

The front end in FIG. 18 shows, outside of the housing 12 of the rotary damper 1, a mechanical stopper 64 which mechanically limits the feasible pivoting range to protect the swiveling vanes inside against damage.

The magnetic field source 8 in the housing part 22 presently consists of electric coils 9 each being annular and accommodated in the housing part 22. In this exemplary embodiment both of the end parts are provided with electric coils 9. A controller may predetermine the magnetic field strength.

Two partition units 4 protrude radially inwardly from the housing into the damper volume 60. The partition units 4 form partition walls and thus delimit the feasible rotary motion of the damper shaft 3 on which two partition units 5 are also configured which protrude radially outwardly from the damper shaft. Rotating the damper shaft 3 swivels the partition walls 5 which thus form swiveling vanes. The chambers 61 and 61a are reduced accordingly (see FIG. 19) or increased again.

Figure 19:
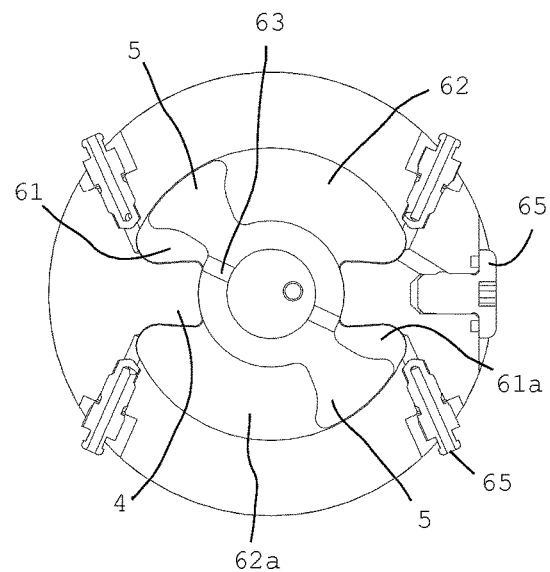
FIG. 19 a cross-section of the rotary damper of the prosthesis device of FIG. 18.

FIG. 19 also shows four air relief valves inserted in a prototype to achieve faster filling and draining and (all of) which may not have to be realized.

Figure 20:
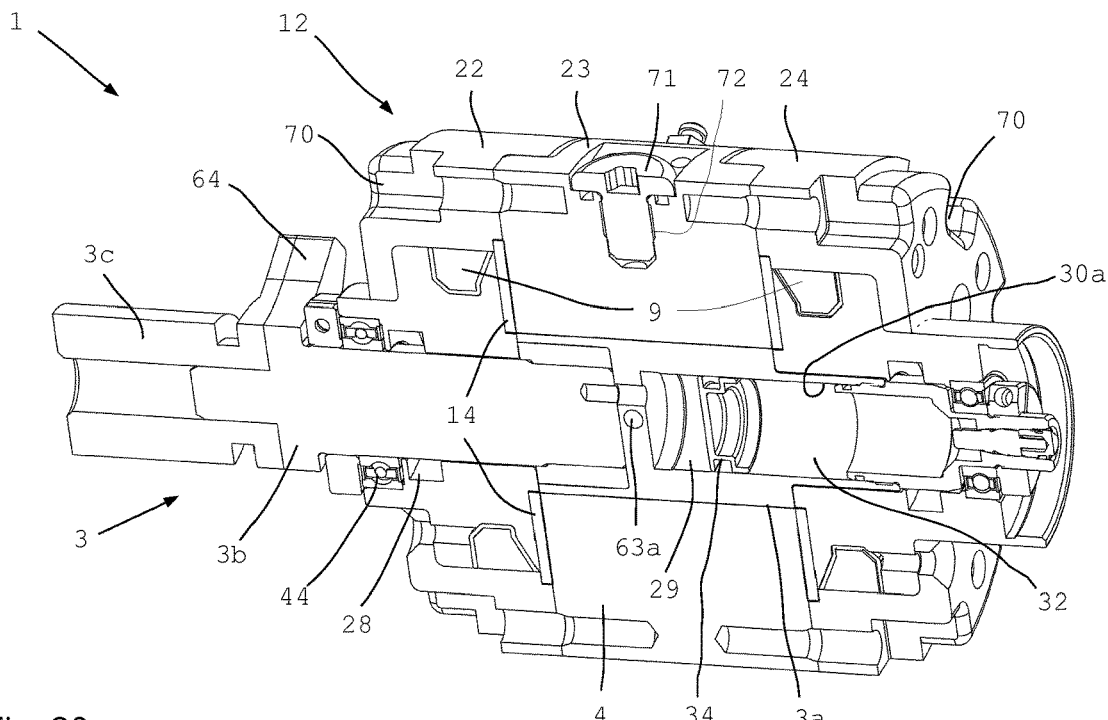
FIG. 20 a longitudinal section of the rotary damper of the prosthesis device of FIG. 18.
Figure 21:
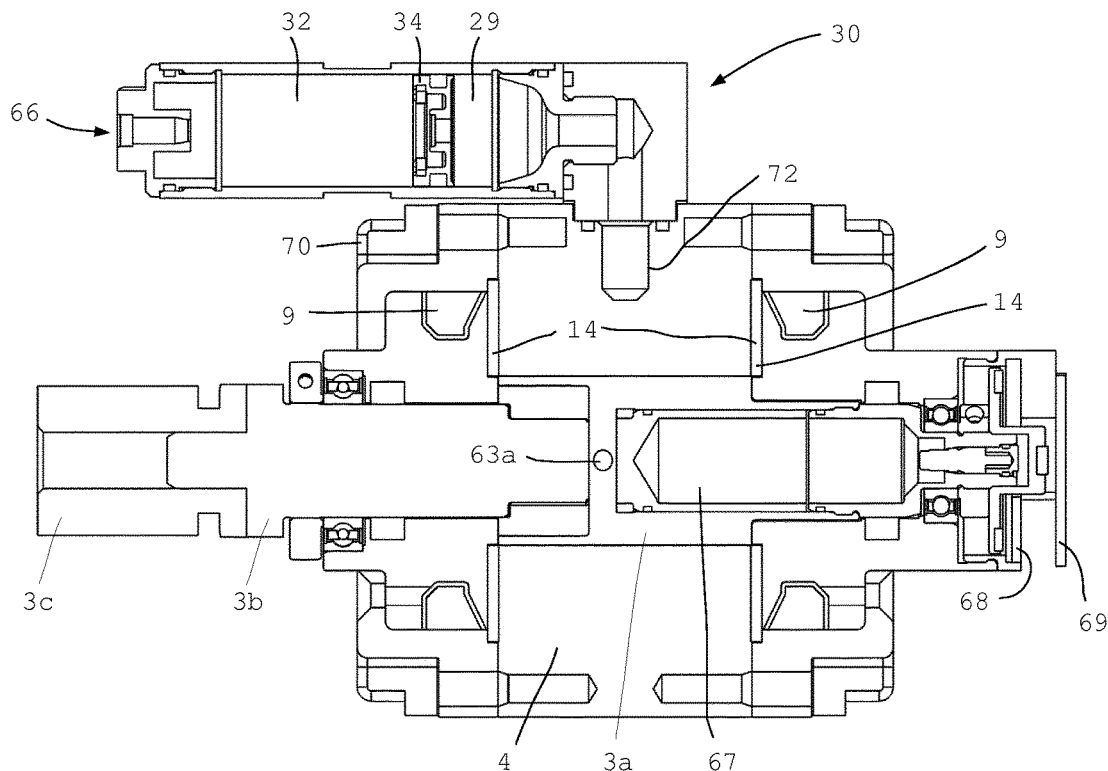
FIG. 21 an alternative embodiment of the rotary damper of the prosthesis device of FIG. 18.

As FIG. 20 also shows, the electric coils 9 in this exemplary embodiment are radially disposed radially relatively far outwardly and are axially inwardly delimited by a ring 20 that is magnetically non-conductive or poorly conductive and serves to form the magnetic field curve. The ring 20 has in particular a hollow cylindrical shape.

In the complete longitudinal section according to FIG. 20 the equalizing device 30 can be seen which is accommodated in the interior of the damper shaft 3. The equalizing device 30 comprises an equalizing volume 29 filled with MRF, which is separated from the air chamber 32 by a movably disposed dividing piston 34. Both the air chamber 32 and also the dividing piston 34 and the equalizing volume 29 are accommodated inside a hollow cylindrical takeup space 30a entirely in the interior of the damper shaft 3. The hollow cylinder 30a is closed at the axially outwardly end by a top with the valve 66. This configuration allows a particularly compact, space-saving structure with only very few parts protruding from the rotary damper 1 which is generally substantially cylindrical. This increases the range of options as to installation and application of these kinds of prosthesis device 100.

In FIGS. 18 to 20 the equalizing device 30 is connected through ducts (not shown) with the duct 72 which is closed by a cover 71. This allows to optionally couple an external equalizing device 30 and to insert an insert member in the interior to largely fill the volume of the hollow cylinder 30a. This allows e.g. a particularly wide range of temperature compensation. It is also possible to ensure particularly long operating times even if some leakage occurs.

FIG. 20 clearly shows the presently tripartite damper shaft 3 consisting of the hollow shaft 3a, the junction shaft 3b and the projection 3c. The three parts are non-rotatably coupled with one another. It is also possible to configure the damper shaft 3 in two parts or in one piece only.

FIG. 21 shows a variant of the exemplary embodiment according to FIGS. 18 to 20 with a coupled external equalizing device 30. The further components may be identical. The rotary damper 1 according to FIG. 18 virtually allows to remove the cover 71 and to screw on the illustrated external equalizing device. In the interior an air or fluid chamber 32 is configured separated by a dividing piston 34 from the equalizing volume 29 filled with MRF.

In the interior of the hollow cylinder 30a an insert member 67 is accommodated to void-fill the volume.

In the exemplary embodiment according to FIG. 21 two angle sensors 68 and 69 are attached as well. An angle sensor 68 providing reduced precision measures the absolute angular position and the angle sensor 69 providing enhanced precision, a relative angular position. This allows to provide a high-precision sensor system which is rugged and reliable and still works with high precision.

Overall, an advantageous prosthesis device 100 with a rotary damper 1 is provided. In order to allow compensation of the temperature-induced volume expansion of the MR-fluid (MRF) and the adjacent components, it is useful to provide an adequate equalizing volume.

In a specific case ca. 50 ml MRF per single actuator or rotary damper is required and thus ca. 150 ml for the entire system. The prestressing member is preferably a nitrogen volume that is in particular prestressed at ca. 75 bar.

In this example a coil wire having an effective cross-section of 0.315 mm$^2$ was used. The number of turns of 400 showed a cable fill factor of ca. 65% with 16 ohm resistance. A larger wire diameter allows to obtain a still higher coil speed.

Preferably the axial clearance of the partition walls or swiveling vane is set. For faultless function of the actuator it is advantageous to center and adjust the axial position of the swiveling vane 5 relative to the housing. To this end e.g. threaded adjusting collars may be used which are brought to a central position by means of a dial gauge.

In a specific case MRF was filled up to a filled volume of (just less than) 75 ml MRF. For filling the MRF may be filled through the equalizing volume. By way of reciprocal movement of the swiveling vane the MRF can be distributed within the chambers 61, 62 (pressure space) and any air pockets can be conveyed upwardly. Thereafter the system may be prestressed with nitrogen (ca. 5 bar). Thereafter the deaeration screws 65 on the outside of the housing 12 may be opened to let the trapped air escape. Finally the nitrogen chamber 32 was prestressed to 30 bar for initial tests in the test rig.

For the purpose of optimizing, the actuator of the prosthesis may be taken to a negative pressure environment to better evacuate any air pockets.

High pressures are obtained without any mechanical sealing. The prosthesis device 100 with the rotary damper 1 is inexpensive in manufacture, sturdy and durable.

In this specific example the braking momentum at the test rig was >210 Nm. The unit is smaller in structure, weighs less, and is more cost-effective than in the prior art.

Switching times of <30 ms are possible and have been proven (full load step change).

The braking momentum is variable as desired. No mechanically moving parts are required. Controlling simply occurs by way of varying the electric current or the magnetic field.

A considerable advantage ensues from the absence of mechanical seals. Thus a very low base momentum of beneath 0.5 Nm is achieved. This is achieved by controlling not only the braking momentum but simultaneously also the sealing effect of the seals. On the whole there is a very low power consumption of just a few watts in the example.

The rotary damper 1 may be employed in a variety of prosthesis devices 100. Application as a (partial) hip prosthesis, a knee prosthesis, an artificial foot, elbow, (partial) shoulder prosthesis is possible. A suitably adapted rotary damper 1 may be installed therein. Dimensioning can be matched to the desired forces and moments to be applied. Suitable scaling is possible.

In all the configurations a prosthesis device 100 may be configured as a prosthesis, an orthosis or as an exoskeleton.

LIST OF REFERENCE NUMERALS 1 rotary damper
2 displacing device
3 damper shaft
3a hollow shaft
3b junction shaft
4 partition unit, partition wall
5 partition unit, partition wall
7 control device
8 magnetic field source
9 electric coil
10 magnetic field
11 connection (with 12)
12 housing of 2
12a outwardly housing part
13 connection (with 3)
14 insulator
15 hydraulic line
16 power connection
17 damping duct
19 axis of 3, 9
20 ring in 12
22 first end portion
23 center region
24 second end portion
25 gap, axial gap
26 gap, radial gap
27 gap, radial gap
28 seal at 3
29 equalizing volume
30 compensating device
30a hollow cylinder
31 valve unit
31a valve head
32 air chamber
33 seal
34 dividing piston
35 cap
36 duct
37 energy storage device
39 permanent magnet
40 sensor device
41 distance
42 seal of 23
43 intermediate space
44 bearing
45 load sensor
46 arm
47 spring, torsion bar
48 sensor line
52 valve unit
53 direction of movement
54 pressure accumulator
55 direction of arrow
60 damper volume
61 chamber
62 chamber
63 connection duct
63a second connection duct
64 mechanical stopper
65 deaeration screw
66 nitrogen valve
67 insert member
68 sensor
69 sensor
70 non-round coupling contour
71 cover
72 duct
100 prosthesis device

The invention claimed is:

1. A prosthesis device with a rotary damper comprising:
a housing, a damper shaft rotatably mounted to the said housing, a displacing device in said housing, and at least one magnetic field source;
said displacing device including a damper volume with magnetorheological fluid as a working fluid and configured to influence by way of the magnetorheological fluid a damping of a rotary motion of said damper shaft relative to said housing;
said displacing device including at least two partition units disposed to divide the damper volume into at least two variable chambers, said at least two partition units including a first partition wall connected to said housing and a second partition wall connected to said damper shaft;
wherein a gap section is formed in a radial direction between said first partition wall and said damper shaft;
wherein a gap section is formed in the radial direction between said second partition wall and said housing; and
wherein at least one gap section is formed in the axial direction between said second partition wall and said housing;
wherein said magnetic field source includes two electric coils configured to generate a magnetic field for setting a strength of a damping of said damper shaft, said electric coils being disposed to cause the magnetic field to traverse at least two of said gap sections;
said housing having a first end part accommodating one of said electric coils, a second end part accommodating another of said electric coils, and a center part therebetween, and wherein said electric coils have axes extending substantially parallel to said damper shaft; and
wherein at least a substantial portion of the magnetic field generated by said magnetic field source passes through at least two of said gap sections; and
a ring disposed axially adjacent one of said electric coils in said housing, said ring consisting essentially of a material having a relative permeability of less than 10, said ring being disposed axially between said electric coil and said damper volume.

2. The prosthesis device according to claim 1, wherein at least one of said gap sections is configured as a damping gap and at least one of said gap sections is configured as a sealing gap, and wherein at least one damping gap has a greater gap height than a sealing gap.

3. The prosthesis device according to claim 1, wherein said second partition wall has two axial ends disposed to form an axial gap section between said housing and said second partition wall and wherein a substantial part of the magnetic field of said magnetic field source passes through said two axial gap sections between said housing and said second partition wall and provides for sealing said two axial gap sections.

4. The prosthesis device according to claim 1, wherein the magnetic field is formed to extend transversely to at least one of said gap sections.

5. The prosthesis device according to claim 1, wherein at least one radial gap section is configured as a damping duct and is disposed radially between said second partition wall and said housing and/or wherein at least one axial gap section is configured as a damping duct and is disposed axially between said second partition unit and said housing.

6. The prosthesis device according to claim 5, wherein at least a substantial part of the magnetic field of the magnetic field source passes through said damping duct.

7. The prosthesis device according to claim 1, wherein at least one gap section is sealed by means of a mechanical sealant.

8. The prosthesis device according to claim 1, wherein said housing consists essentially of a magnetically conductive material having a relative permeability of above 100.

9. The prosthesis device according to claim 1, wherein the magnetorheological fluid is conveyed by way of relative pivoting motion of said damper shaft and of said housing through at least one gap section from one chamber into another chamber.

10. The prosthesis device according to claim 1, wherein said at least two partition units include a plurality of second partition walls disposed on said damper shaft and distributed over a circumference thereof and wherein said at least two partition units include a plurality of first partition walls disposed on said housing and distributed over a circumference thereof.

11. The prosthesis device according to claim 10, wherein opposite chambers are connected through at least one connection duct.

12. The prosthesis device according to claim 1, further comprising an equalizing device with an equalizing volume connected with a low pressure chamber and a high pressure chamber through a valve unit, wherein said valve unit is configured to establish a connection between said equalizing volume and said low pressure chamber and to block a connection between said equalizing volume and said high pressure chamber.

13. The prosthesis device according to claim 12, wherein said equalizing device is accommodated in an interior of said damper shaft.

14. The prosthesis device according to claim 1, further comprising a temperature sensor for capturing a temperature of the magnetorheological fluid and/or an angle sensor for capturing a measure for an angular position of said damper shaft and/or a load sensor for capturing a characteristic value of a torque acting on said damper shaft.

15. The prosthesis device according to claim 1, further comprising a control device and at least one sensor unit with at least one position sensor and/or distance sensor for capturing a position and/or a distance from surrounding objects, and wherein said control device is configured to control the rotary damper in dependence on sensor data from said at least one sensor unit.

16. The prosthesis device according to claim 1, comprising a control device and a plurality of interconnected rotary dampers.

17. A prosthesis device with a rotary damper comprising:
a housing, a damper shaft rotatably mounted to the said housing, a displacing device in said housing, and at least one magnetic field source;
said displacing device including a damper volume with magnetorheological fluid as a working fluid and configured to influence by way of the magnetorheological fluid a damping of a rotary motion of said damper shaft relative to said housing;
said displacing device including at least two partition units disposed to divide the damper volume into at least two variable chambers, said at least two partition units including a first partition wall connected to said housing and a second partition wall connected to said damper shaft;
wherein a gap section is formed in a radial direction between said first partition wall and said damper shaft;

wherein a gap section is formed in the radial direction between said second partition wall and said housing; and wherein at least one gap section is formed in the axial direction between said second partition wall and said housing;

wherein said magnetic field source includes two electric coils configured to generate a magnetic field for setting a strength of a damping of said damper shaft, said electric coils being disposed to cause the magnetic field to traverse at least two of said gap sections;

said housing having a first end part accommodating one of said electric coils, a second end part accommodating another of said electric coils, and a center part therebetween, and wherein said electric coils have axes extending substantially parallel to said damper shaft; and wherein at least a substantial portion of the magnetic field generated by said magnetic field source passes through at least two of said gap sections; and a ring disposed axially adjacent one of said electric coils in said housing, said ring, in a radially outward region, having a thinner wall thickness than in a radially inward region and/or wherein said ring consists essentially of a material having a relative permeability of above 50.

18. A prosthesis device with a rotary damper comprising:

a housing, a damper shaft rotatably mounted to the said housing, a displacing device in said housing, and at least one magnetic field source;

said displacing device including a damper volume with magnetorheological fluid as a working fluid and configured to influence by way of the magnetorheological fluid a damping of a rotary motion of said damper shaft relative to said housing;

said displacing device including at least two partition units disposed to divide the damper volume into at least two variable chambers, said at least two partition units including a first partition wall connected to said housing and a second partition wall connected to said damper shaft;

wherein a gap section is formed in a radial direction between said first partition wall and said damper shaft;

wherein a gap section is formed in the radial direction between said second partition wall and said housing; and wherein at least one gap section is formed in the axial direction between said second partition wall and said housing;

wherein said magnetic field source includes two electric coils configured to generate a magnetic field for setting a strength of a damping of said damper shaft, said electric coils being disposed to cause the magnetic field to traverse at least two of said gap sections;

said housing having a first end part accommodating one of said electric coils, a second end part accommodating another of said electric coils, and a center part therebetween, and wherein said electric coils have axes extending substantially parallel to said damper shaft; and wherein at least a substantial portion of the magnetic field generated by said magnetic field source passes through at least two of said gap sections; and an equalizing device with an equalizing volume connected with a low pressure chamber and a high pressure chamber through a valve unit, wherein said valve unit is configured to establish a connection between said equalizing volume and said low pressure chamber and to block a connection between said equalizing volume and said high pressure chamber.

* * * * *